United States Patent [19]

Reeders et al.

[11] Patent Number: 5,424,408
[45] Date of Patent: Jun. 13, 1995

[54] α-3 CHAIN TYPE IV COLLAGEN POLYNUCLEOTIDES

[75] Inventors: Stephen T. Reeders, Hamden, Conn.; Karen E. Morrison, Cambridge, England; Billy G. Hudson, Lenexa, Kans.

[73] Assignees: Yale University, New Haven, Conn.; The University of Kansas Medical Center, Kansas City, Kans.

[21] Appl. No.: 621,091

[22] Filed: Nov. 30, 1990

[51] Int. Cl.⁶ ............................................. C12N 15/12
[52] U.S. Cl. ..................................... 536/23.5; 530/356
[58] Field of Search ................ 536/27, 23.5; 435/69.3; 530/356

[56] References Cited

U.S. PATENT DOCUMENTS 4,394,443  7/1983  Weissman et al. ..................... 435/6
4,800,159  1/1989  Mullis et al. ....................... 435/172.3

OTHER PUBLICATIONS

Butkowski et al, *J. Lab. Clin Med.,* 115, (1990), pp. 365–373 "Characterization of type IV collagen NC1 monomers and Goodpasture antigen in human renal basement membranes".

Saus et al, *The Journal of Biological Chemistry,* 263, (1988), pp. 13374–13380, "Identification of the Goodpasture Antigen as the α (IV) Chain of Collagen IV".

Morrison et al, *The Journal of Biological Chemistry,* 266, (1991), pp. 34–39, "Use of the Polymerase Chain Reaction to Clone and Sequence a cDNA Encoding the Bovine α2 Chain of Type IV Collagen".

Dion et al, *J. Mol. Biol.,* (1987) 193, pp. 127–143, "COOH-terminal Propeptides of the Major Human Procollagens Structural, Functional and Genetic Comparisons".

Erkki Soini et al, *Clinical Chemistry,* vol. 25, No. 3, 1979 pp. 353–361, "Fluoroimmunoassay: Present Status and Key Problems".

Taina Pihlajaniemi et al, *The Journal of Biological Chemistry,* vol. 265, No.23, pp. 13758–13766, 1990, "Complete Primary Structure of the Triple-helical Region and the Carboxyl-terminal Domain of a New Type IV Collagen Chain, α5(IV)".

Feinberg et al, *Analytical Biochemistry,* 132, pp. 6–13 (1983), "A Technique for Radiolabeling DNA Restriction Endonuclease Fragments to High Specific Activity".

McCoy et al, *Kidney International,* vol (1982), pp. 642–652, "Absence of nephritogenic GBM antigen(s) in some patients with hereditary nephritis".

Brinker et al, *Proc. Natl. Acad. Sci. USA,* vol. 82, pp. 3649–3653, Jun. 1985, Biochemistry, "Restricted homology between α1 type IV and other procollagen chains".

U. K. Laemmli, *Nature,* vol. 227, (1970) "Cleavage of Structural Proteins during the Assembly of the Head of Bacteriophage T4" pp. 680–685.

Piotr Chomzczynski et al, *Analytical Biochemistry,* 162, pp. 156–159, "Single-Step Method of RNA Isolation by Acid Guanidinium Thiocyanate-Phenol-Chloroform Extraction".

Timpl et al, *J. Biochem.,* 120, pp. 203–211, (1981), "A Network Model for the Organization of Type IV Collagen Molecules in Basement Membranes".

(List continued on next page.)

*Primary Examiner*—Charles L. Patterson, Jr
*Attorney, Agent, or Firm*—Frishauf, Holtz, Goodman & Woodward

[57] ABSTRACT

An isolated and substantially pure polynucleotide encoding 238 amino acids of the carboxy terminal end of the triple helical domain and all 233 amino acids of the carboxy terminal noncollageneous domain of the bovine α3 chain of type IV collagen. An isolated and substantially pure polynucleotide encoding 218 amino acids of the carboxy terminal noncollagenous domain of the human α3 chain of type IV collagen. Such polynucleotides are useful to express large amounts of proteins in vectors and such expressed proteins are useful to detect Goodpasture antibodies in blood and to remove Goodpasture antibodies from the bloodstream of patients suffering from Goodpasture syndrome.

4 Claims, 7 Drawing Sheets

OTHER PUBLICATIONS

Martin et al, *Advances in Protein Chemistry*, vol. 39, (1988) pp. 1–51, "Basement Membrane Proteins: Molecular Structure and Function".

Timpl, *Eur. J. Biochem.* 180, 487–502 (1989), "Structure and Biological activity of basement membrane proteins".

Hostikka et al, *The Journal of Biological Chemistry*, vol. 263, No. 36, (1988), pp. 19488–19493, "The Complete Primary Structure of the α2 Chain of Human Type IV Collagen and Comparison with the α1(IV) Chain".

Muthukumaran et al, *The Journal of Biological Chemistry*, vol. 264, No. 11 (1989) pp. 6310–6317, "The Complete Primary Structure for the α1-Chain of Mouse Collagen IV".

Saus et al, *The Journal of Biological Chemistry*, vol. 264, (1989), pp. 6318–6324, "The Complete Primary Structure of Mouse α2(IV) Collagen".

Blumberg et al, *The Journal of Biological Chemistry*, vol. 263, No. 34, (1988), pp. 18328–18337, "Drosophila Basement Membrane procollagen α1(IV)".

Butkowski et al, *The Journal of Biological Chemistry*, vol. 260, No. 6, (1985), pp. 3739–3747, "Properties of the Globular Domain of Type IV Collagen and Its Relationship to the Goodpasture Antigen".

Wieslander et al, *The Journal of Biological Chemistry*, vol. 260, No. 260, No. 14, (1985), pp. 8564–8570, "Physical and Immunochemical Studies of the Globular Domain of Type IV Collagen".

Butkowski et al, *The Journal of Biological Chemistry*, vol. 262, No. 16, (1987) pp. 7874–7877, "Localization of the Goodpasture Epitope to a Novel Chain of Basement Membrane Collagen".

Hudson et al. *Laboratory Investigation*, vol. 61, No. 3 pp. 256–269, (1989), "Biology of Disease Goodpasture Syndrome: Molecular Architecture and Function of Basement Membrane Antigen".

Kleppel et al, *The Journal of Biological Chemistry*, vol. 261, No. 35, (1986), pp. 16547–16552, "Antibody Specificity of Human Glomerular Basement Membrane Type IV Collagen NC1 Subunits".

Jeraj et al, *American Journal of Kidney Diseases*, vol. 11 No. 6, (1983), "Absence of Goodpasture's Antigen in Male Patients With Familial Nephritis".

Kashtan et al, *J. Clin. Invest.*, vol. 78, (1986), pp. 1035–1044, "Nephritogenic Antigen Determinants in Epidermal and Renal Basement Membranes of Kindreds with Alport-type Familial Nephritis".

Jenis et al, *Clinical Nephrology*, vol. 15, No. 3 (1981) pp. 111–114, "Variability of anti-GBM binding in hereditary nephritis".

Olson et al, *The Journal of Pediatrics*, vol. 96, (1990) pp. 697–699, "Diagnosis of Hereditary nephritis by failure of glomeruli to bind anti-glomerular basement membrane antibodies".

Savage et al, *Kidney International*, vol. 30, (1986) pp. 107–112, "The Goodpasture antigen in Alport's syndrome: Studies with a monoclonal antibody".

Hostikka et al, *Proc. Natl. Acad. Sci, USA*, vol. 87, (1990) pp. 1606–1610, "Identification of a distinct type IV collagen α chain with restricted kidney distribution and assignment of its gene to the locus of X chromosome—linked Alport syndrome".

Myers et al, *Am. J. Hum. Genet.*, 46:1024–1033, (1990), pp. 1024–1033, "Molecular Cloning of α5(IV) Collagen and Assignment of the Gene to the Region of the X Chromosome Containing the Alport Syndrome Locus".

Atkin et al, *Am. J. Hum. Genet.*, 42:249–255, (1988), pp. 249–255, "Mapping of Alport Syndrome to the Long Arm of the X Chromosome".

Brunner et al, *Kidney International*, vol. 34, (1988), pp. 507–510, "Localization of the gene for X-linked Alport's syndrome".

Flinter et al, *Genomics*, vol. 4, pp. 335–338 (1989), "Localization of the Gene for Classic Alport Syndrome".

Barker et al, *Science*, vol. 248, pp. 1224–1227, (1990), "Identification of Mutations in the COL4A5 Collagen Gene in Alport Syndrome".

Pihlajaniemi et al, *The Journal of Biological Chemistry*, vol. 260, No. 12, (1985), pp. 7681–7687, "cDNA Clones Coding for the Pro-α1 (IV) Chain of Human Type IV Procollagen Reveal an Unusual Homology of Amino Acid Sequences in Two Halves of the Carboxyl-terminal Domain".

Gunwar et al, *The Journal of Biological Chemistry*, vol. 265, No. 10, (1990), pp. 5466–5469, "Glomerular Basement Membrane".

Grunfeld, *Kidney International*, vol. 27, (1985), pp. 83–92, "The clinical spectrum of hereditary nephritis".

Hinglais, et al, *Laboratory Investigation*, vol. 27, (1972)

(List continued on next page.)

OTHER PUBLICATIONS

No. 5, pp. 473–487, "Characteristic Ultrastructural Lesion of the Glomerular Basement Membrane in Progressive Hereditary Nephritis (Alport's Syndrome".

Yoshikawa et al, *J. Pathology*, vol. 135, (1981), 199–209, "The Glomerular Basal Lamina in Hereditary Nephritis".

Henry et al, *Clinical Chemistry*, vol. 22, No. 7, 1976, p. 1232, "Debate on the Procedure of Rao et al for Creatine Kinase".

S. Szpiro-Tapia et al, *Hum. Genet.*, (1988) vol. 81, pp. 85–87, "Linkage studies in X-linked Alport's syndrome".

Kleppel et al, *J. Clin. Invest.*, vol. 80, (1987), pp. 263–265, "Alport Familial Nephritis Absence of 28 Kilodalton Non-Collagenous Monomers of Type IV Collagen in Glomerular Basement Membrane".

Soininen et al, *Febs Letters*, vol. 225, No. 1,2, pp. 188–194, (1987), "Complete primary structure of the $\alpha_1$-chain of human basement membrane (type IV) collagen".

M$_2$ = GOOD PASTURE ANTIGEN
α3 NCI MONOMER.

FIG. 7

| | | |
|---|---|---|
| F1: | 5' - AAGCCNGGNGA(C,T)ACAGG - 3' | (5) |
| F2: | 5' - AAGCCNGGNGA(C,T)ACCGG - 3' | (5) |
| F3: | 5' - AAGCCNGGNGA(C,T)ACGGG - 3' | (5) |
| F4: | 5' - AAGCCNGGNGA(C,T)ACTGG - 3' | (5) |
| R1: | 5' - TA(A,G)TG(T,C)CTNGT(A,G)AANACAAA - 3' | (28) |
| R2: | 5' - TA(A,G)TG(T,C)CTNGT(A,G)AANACGAA - 3' | (28) |
| R3: | 5' - TA(A,G)TGNCGNGT(A,G)AANACAAA - 3' | (28) |
| R4: | 5' - TA(A,G)TGNCGNGT(A,G)AANACGAA - 3' | (28) |
| | | |
| FA: | 5' - GCNGGNCGNGTNATGCG - 3' | (14) |
| FB: | 5' - GCNGGNCGNGTNATGAG - 3' | (14) |
| FC: | 5' - GTNTT(C,T)ACNAG(A,G)CA(C,T)TATC - 3' | (22) |
| FD: | 5' - CCAGG(A,C)GA(C,T)AC(A,C,T)GGNCC(A,C,T)CCAG - 3' | (6) |
| RA: | 5' - CAGGAAGGGCAT(G,T)GTGCTGAA - 3' | [165] |
| RB: | 5' - GG(G,C)GCCTCACACACAG(A,C)ACA - 3' | [317] |
| RC: | 5' - TTGCAG(A,T)ACAGGAAGGGCAT - 3' | [173] |
| RD: | 5' - TTGCAG(A,T)ACAGGAAGGG - 3' | [173] |
| | | |
| F9*: | 5' - CCCGATGGGTTGCCAGGATCCAT - 3' | [-42] |
| R9*: | 5' - TGACTATGCCTGGTCACAAG - 3' | [37] |

α-3 CHAIN TYPE IV COLLAGEN POLYNUCLEOTIDES

GOVERNMENT RIGHTS

This invention was made with United States government support under Grants DK40703 and DK 18381 from the National Institute of Health. The United States government has certain rights in this invention.

BACKGROUND OF THE INVENTION

1. Field of the Invention

The present invention concerns alpha-3 chain type IV bovine and human polynucleotides and peptides expressed by such polynucleotides which are useful in detecting Goodpasture antibodies and treating Goodpasture syndrome.

2. Background Information

The major structural component of mammalian basement membranes, type IV collagen, is composed of a number of distinct polypeptide chains (Timpl et al. 1981; Martin et at 1988; Timpl 1989). The most abundant species, α1(IV) and α2(IV) have been extensively characterized in man and mouse and an α type chain from Drosophila also been identified (Soinimen et al. 1987; Blumberg et al. 1988; Hostikka and Tryggvason 1988; Saus et al. 1989; Muthukumaran et al. 1989). Characteristics of these collagens include a highly conserved carboxy-terminal noncollagenous (NC1) domain of ~229 residues, a shorter amino-terminal globular domain (7S domain) and a triple helical collagenous domain, in which interruptions occur in the Gly-Xaa-Xaa-Yaa repeat motif, giving a degree of flexibility to the triple helix. Within the membrane matrix the individual collagen chains exist as heterotrimer, which form a supra-molecular structure via interactions between the 7S domains of 4 molecules and the NCI domains of 2 heterotrimers (Timpl et at 1981).

Bacterial collagenase digestion releases the NCI domains from the other components of basement membrane as hexamers, comprised of the 3 NC1 domains from each of 2 interacting collagen heterotrimers. The NCI domains can be further separated on the basis of molecular weight by denaturing polyacrylamide gel electrophoresis. This results in a number of separate monomeric and dimeric subunits (Mr=24,500–28,300 and 40,000–50,7000 respectively), including several which are distinct from the α1(IV) and α2(IV) chains (Butkowski et al. 1985; Wieslander et al. 1985). The monomeric subunits that result from collagenase digestion of human glomerular basement membrane (GBM) have been termed M24, M26, M28+++ and M28+, while the equivalent subunits of bovine basement membranes have been termed Mla, Mlb, M2, and M3 (Kleppel et al. 1986; Butkowski et al. 1987). M24 (or M1a) and M26 (or M1b) are the NC1 domains of the α1(IV) and α2(IV) chains. M28+++ (or M2*) and M28+ (or M3) are the NCI domains of 2 novel collagen chains termed α3(V) and α4(V). Short segments of the junction between the collagenous and NCI domains of human and bovine α3(IV) and α4(IV) peptides have been sequenced, confirming that they have a type IV collagen structure (Saus et at 1988; Butkowski et al. 1990).

The α3(IV) chain and the α4(IV) chain are of particular interest as such chains have been implicated in the pathogenesis of Goodpasture syndrome and Alport-type familial nephritis, clinical syndromes that affect GBM and cause functional kidney impairment (Hudson et al. 1989). Goodpasture syndrome is an autoimmune disorder characterized by glomerulonephritis, lung hemorrhage and anti-GBM antibody formation (Glassock et al. 1986). The nephritis and lung damage are mediated by these anti-GBM antibodies which are primarily targeted at the NCl domain (M28+++) of α3(IV) (Butkowski et al 1985; Wieslander et al. 1985; Kleppel al.1986). Alport syndrome is an inheritable disorder characterized by glomerulonephritis, sensorineural hearing loss and various abnormalities of the lens of the eye (Grunfeld, 1985). Ultrastructural GBM abnormalities frequently observed in the syndrome include thinning, diffuse splitting and multilamination of the lamina dense (Hinglais et al. 1972; Yoshikawa et al. 1981). Several investigators have reported that the GBM of some individuals with Alport syndrome does not react in vitro with Goodpasture antibodies nor with a monoclonal antibody that recognizes a Goodpasture epitope, suggesting that there is an abnormality of the α3(IV) chain in these patients (Olsen et at 1980; Jenis et al. 1981; Jeraj et al. 1983; Kashtan et al. 1986; Savage et at 1986; Kleppel et al. 1987).

Recently a gene encoding another novel human type IV collagen chain, COL4A5, was cloned, on the basis of homology with the α1(IV) and α2(IV) chains (Hostikka et al. 1990; Myers et al. 1990). The existence of such a chain had not been expected from biochemical or immunological studies of GBM (glomerular basement molecular), and yet antibodies raised to a peptide fragment synthesized from the predicted amino acid sequence of α5(IV) localized this chain to the GBM (Hostikka et at 1990). COL4A5 maps to Xq22, a region known from genetic linkage studies to contain a locus for Alport Syndrome (Atkin et al. 1988; Brunner et al. 1988; Flinter al. 1988). Further, COL4A5 has been shown to be mutated in 3 of 18 large kindreds with the disease (Barker et al. 1990).

SUMMARY OF THE INVENTION

The present invention concerns an isolated and substantially pure polynucleotide encoding 238 consecutive amino acids from the carboxy terminal end of the triple helical domain and all 233 amino acids of the carboxy terminal noncollageneous domain of the bovine α3 chain of type IV collagen and a nucleotide sequence of said polynucleotide. The invention is also directed to a deduced amino acid sequence of the bovine α3 chain of type IV collagen.

The present invention also relates to an isolated and substantially pure polynucleotide encoding 218 consecutive amino acids of the carboxy terminal noncollagenous domain of the human α3 chain of type IV collagen and a nucleotide sequence of said polynucleotide. The invention is also directed to a deduced amino acid sequence of the human α3 chain of the type IV collagen.

The above described polynucleotides can be used to express large amounts of proteins in vectors. Such proteins can be used to detect Goodpasture antibodies from the bloodstream of patients suffering from Goodpasture syndrome.

The present invention also concerns a peptide having no more than 218 amino acids of the human α3 chain of type IV collagen comprising the following amino acid sequence:

ISRCQVCMKKRH (Iso Ser Arg Cys Gln Val Cys Met Lys Lys Arg His) (SEQ ID NO: 3).

The invention also relates to 6 to all 12 consecutive amino acids of the sequence ISRCQVCMKKRH (SEQ ID NO: 3).

The invention also relates to a method for detecting Goodpasture antibodies from a bodily fluid or tissue from a patient, for example, a human, comprising contacting a bodily fluid or tissue from the patient, for example, a human, for example, contacting blood or a liquid fraction thereof, e.g. serum or plasma, with a peptide having no more than 218 amino acids of the human α3 chain of type IV collagen comprising the following amino acid sequence: ISRCQVCMKKRH (SEQ ID NO: 3), whereby if Goodpasture antibodies are present a product will form of the antibodies and peptide and detecting for the presence of Goodpasture antibodies by, for example, by labelling the peptide, e.g., using an ELISA technique, i.e., using an enzyme label and detecting for the presence of the label on the antibody-peptide product.

The present invention is further directed to a therapeutic method of treating Goodpasture syndrome in a patient by neutralizing Goodpasture antibodies in the whole blood or liquid fraction thereof, e.g., plasma or serum, of the patient, for example, a human patient, by contacting the whole blood or liquid fraction thereof from the patient with an effective antibody neutralizing amount of a peptide having no more than 218 amino acids of the human α3 chain of type IV collagen comprising the following amino acid sequence: ISRCQVCMKKRH (SEQ ID NO: 3). In such therapeutic method, the peptide is preferably bound to a solid support and the blood, serum or plasma from the patient passes over the peptide bound to the solid support, whereby the peptide captures the Goodpasture antibodies to remove such antibodies from the patient's blood, serum or plasma. The blood, serum or plasma with some, all or most of the Goodpasture antibodies removed is then returned to the bloodstream of the patient intravenously.

BRIEF DESCRIPTION OF THE DRAWINGS

FIG. 7 depicts oligonucleotide primer sequences. N is A or C or G or T. Numbers in parentheses at the right indicate the number of the α3(IV) amino acid from which the 5' end of the nucleotide sequence was derived. The α3(IV) amino acid sequence is from reference 13, numbering the first glycine residue of M2* as 1. Numbers in brackets at the right indicate the number of the α1(IV) nucleotide from which the 5' end of the nucleotide sequence was derived. The α1(IV) sequence is from reference 29.

Figure 1:
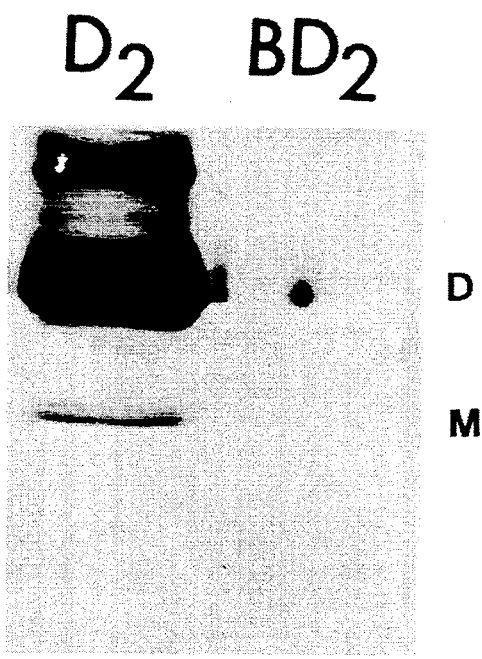
FIG. 1 is a Western blot of dimer fraction D2 (referred to in FIG. 1 as D2) and NC1 hexamer before and after biotinylation samples. After biotinylation, reactivity of dimer fraction D2 with GP-antibodies is lost. Biotinylation of the native NC1 domain does not affect its reactivity with GP-antibodies indicating that the GP-epitope is sequestered inside the hexamer as previously found.

The corresponding SEQ ID NOS. for the sequence in FIG. 7 are as follows:

| | SEQUENCE | SEQ ID NO. |
|---|---|---|
| F1: | 5'-AAGCCNGGNGA(C,T)ACAGG-3' | 4 |
| F2: | 5'-AAGCCNGGNGA(C,T)ACCGG-3' | 5 |
| F3: | 5'-AAGCCNGGNGA(C,T)ACGGG-3' | 6 |
| F4: | 5'-AAGCCNGGNGA(C,T)ACTGG-3' | 7 |
| R1: | 5'-TA(A,G)TG(T,C)CTNGT(A,G)AANACAAA-3' | 8 |
| R2: | 5'-TA(A,G)TG(T,C)CTNGT(A,G)AANACGAA-3' | 9 |
| R3: | 5'-TA(A,G)TGNCGNGT(A,G)AANACAAA-3' | 10 |
| R4: | 5'-TA(A,G)TGNCGNGT(A,G)AANACGAA-3' | 11 |
| FA: | 5'-GCNGGNCGNGTNATGCG-3' | 12 |
| FB: | 5'-GCNGGNCGNGTNATGAG-3' | 13 |
| FC: | 5'-GTNTT(C,T)ACNAG(A,G)CA(C,T)TATC-3' | 14 |
| FD: | 5'-CCAGG(A,C)GA(C,T)AC(A,C,T)GGNCC(A,C,T)CCAG-3' | 15 |
| RA: | 5'-CAGGAAGGGCAT(G,T)GTGCTGAA-3' | 16 |
| RB: | 5'-GG(G,C)GCCTCACACACAG(A,C)ACA-3' | 17 |
| RC: | 5'-TTGCAG(A,T)ACAGGAAGGGCAT-3' | 18 |
| RD: | 5'-TTGCAG(A,T)ACAGGAAGGG-3' | 19 |
| F9*: | 5'-CCCGATGGGTTGCCAGGATCCAT-3' | 20 |
| R9*: | 5'-TGACTATGCCTGGTCACAAG-3' | 21 |

SEQUENCE LISTING ( 1 ) GENERAL INFORMATION:

( i i i ) NUMBER OF SEQUENCES: 23

( 2 ) INFORMATION FOR SEQ ID NO: 1:

( i ) SEQUENCE CHARACTERISTICS:
        ( A ) LENGTH: 1416 base pairs
        ( B ) TYPE: Nucleic acid
        ( C ) STRANDEDNESS: Double
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Calf
        ( B ) STRAIN: Unknown
        ( C ) INDIVIDUAL ISOLATE: Unknown
        ( D ) DEVELOPMENTAL STAGE: Unknown
        ( G ) CELL TYPE: Whole kidney ( v i i ) IMMEDIATE SOURCE:
        ( A ) LIBRARY: Bovine lens cDNA
        ( B ) CLONE: KMC15

( v i i i ) POSITION IN GENOME: Not known
        ( A ) CHROMOSOME/SEGMENT: Not known ( x ) PUBLICATION INFORMATION: None ( x i ) SEQUENCE DESCRIPTION: SEQ ID NO: 1:

```
ggc  ctc  cct  ggc  agg  aaa  ggg  cca  gtg  gga  gat  gct  ggg  cct  c
Gly  Leu  Pro  Gly  Arg  Lys  Gly  Pro  Val  Gly  Asp  Ala  Gly  Pro  P
5                        10                       15
cag  ctt  ggc  gtg  aca  gga  cct  caa  ggg  gca  cca  ggc  ttt  cct  g
Gln  Leu  Gly  Val  Thr  Gly  Pro  Gln  Gly  Ala  Pro  Gly  Phe  Pro  G
20                       25                       30
acc  atc  cct  ggc  cag  aaa  gga  gat  cga  ggt  cca  cct  ggc  tcc  a
Thr  Ile  Pro  Gly  Gln  Lys  Gly  Asp  Arg  Gly  Pro  Pro  Gly  Ser  A
35                       40                       45
aac  cca  ggc  atg  cct  ggt  cct  cct  gga  cct  cca  ggg  agt  cct  g
Asn  Pro  Gly  Met  Pro  Gly  Pro  Pro  Gly  Pro  Pro  Gly  Ser  Pro  V
50                       55                       60
ggc  ata  aaa  gga  gac  aag  ggg  ttg  atg  gga  gag  cct  ggc  caa  a
Gly  Ile  Lys  Gly  Asp  Lys  Gly  Leu  Met  Gly  Glu  Pro  Gly  Gln  A
65                       70                       75
cca  cct  gga  gct  ata  gga  gac  atg  ggg  tca  cca  ggt  cat  ccg  g
Pro  Pro  Gly  Ala  Ile  Gly  Asp  Met  Gly  Ser  Pro  Gly  His  Pro  G
85                       90                       95
cca  ggt  gtc  ccc  ggt  cag  cca  ggg  gcc  aga  ggt  gat  cct  gga  t
Pro  Gly  Val  Pro  Gly  Gln  Pro  Gly  Ala  Arg  Gly  Asp  Pro  Gly  P
100                      105                      110
gga  ttt  cca  ggc  atg  aaa  ggg  aag  aag  ggt  aat  tca  gga  ttt  c
Gly  Phe  Pro  Gly  Met  Lys  Gly  Lys  Lys  Gly  Asn  Ser  Gly  Phe  P
115                      120                      125
cca  cct  gga  cct  cca  ggg  caa  agt  gga  cca  aaa  gga  cca  cct  g
Pro  Pro  Gly  Pro  Pro  Gly  Gln  Ser  Gly  Pro  Lys  Gly  Pro  Pro  G
130                      135                      140
cgt  gga  gag  cct  ggc  aca  gtg  aag  atc  atc  tcc  ctt  cca  gga  a
Arg  Gly  Glu  Pro  Gly  Thr  Val  Lys  Ile  Ile  Ser  Leu  Pro  Gly  S
145                      150                      155
ggc  cca  cct  ggt  tca  gct  gga  gaa  cca  ggg  atg  caa  gga  gaa  c
Gly  Pro  Pro  Gly  Ser  Ala  Gly  Glu  Pro  Gly  Met  Gln  Gly  Glu  P
165                      170                      175
ccc  cca  gga  cca  cca  gga  gat  cca  gga  ccc  tgt  ggg  cca  aaa  g
Pro  Pro  Gly  Pro  Pro  Gly  Asp  Pro  Gly  Pro  Cys  Gly  Pro  Lys  G
180                      185                      190
cca  ggg  gag  gat  ggt  cca  cca  gga  act  cct  gga  cca  act  gga  g
Pro  Gly  Glu  Asp  Gly  Pro  Pro  Gly  Thr  Pro  Gly  Pro  Thr  Gly  G
195                      200                      205
ggc  aac  aaa  ggt  tgt  aaa  gga  gag  caa  gga  cca  cct  gga  tcc  g
Gly  Asn  Lys  Gly  Cys  Lys  Gly  Glu  Gln  Gly  Pro  Pro  Gly  Ser  A
210                      215                      220
ctg  cca  ggc  ttg  aag  ggg  aaa  cct  gga  gac  act  gga  cca  cct  g
```

|  |  |  |  |  |  |  |  |  |  |  |  |  |
|---|---|---|---|---|---|---|---|---|---|---|---|---|
|  | Leu<br>225 | Pro | Gly | Leu | Lys | Gly<br>230 | Lys | Pro | Gly | Asp | Thr<br>235 | Gly | Pro | Pro | A |
| ggg | gca | gtg | atg | agg | ggc | ttt | gtc | ttt | acc | cgg | cac | agc | cag | a |
| Gly<br>245 | Ala | Val | Met | Arg | Gly<br>250 | Phe | Val | Phe | Thr | Arg<br>255 | His | Ser | Gln | T |
| gca | att | ccc | tcc | tgt | cca | gaa | ggg | aca | gag | ccg | ctc | tat | agt | g |
| Ala<br>260 | Ile | Pro | Ser | Cys | Pro<br>265 | Glu | Gly | Thr | Glu | Pro<br>270 | Leu | Tyr | Ser | G |
| tct | ctt | ctc | ttt | gta | caa | gga | aat | gaa | caa | gcc | cat | gga | cag | g |
| Ser<br>275 | Leu | Leu | Phe | Val | Gln<br>280 | Gly | Asn | Glu | Gln | Ala<br>285 | His | Gly | Gln | A |
| gga | aca | ctt | ggc | agc | tgc | ctg | cag | cga | ttt | acc | aca | atg | cca | t |
| Gly<br>290 | Thr | Leu | Gly | Ser | Cys<br>295 | Leu | Gln | Arg | Phe | Thr<br>300 | Thr | Met | Pro | P |
| ttc | tgc | aat | atc | aac | gat | gta | tgt | aat | ttt | gca | tct | cga | aac | g |
| Phe<br>305 | Cys | Asn | Ile | Asn | Asp<br>310 | Val | Cys | Asn | Phe | Ala<br>315 | Ser | Arg | Asn | A |
| tca | tac | tgg | ctg | tca | aca | cca | gct | atg | ata | cca | atg | gac | atg | g |
| Ser<br>325 | Tyr | Trp | Leu | Ser | Thr<br>330 | Pro | Ala | Met | Ile | Pro<br>335 | Met | Asp | Met | A |
| att | act | ggc | agg | gcc | ctg | gag | cct | tat | att | agc | aga | tgt | aca | g |
| Ile<br>340 | Thr | Gly | Arg | Ala | Leu<br>345 | Glu | Pro | Tyr | Ile | Ser<br>350 | Arg | Cys | Thr | V |
| gaa | ggt | cct | gca | att | gcc | ata | gct | gtt | cac | agc | caa | acc | act | g |
| Glu<br>355 | Gly | Pro | Ala | Ile | Ala<br>360 | Ile | Ala | Val | His | Ser<br>365 | Gln | Thr | Thr | A |
| ccc | ccc | tgt | cct | gct | ggc | tgg | att | tct | ctc | tgg | aaa | ggc | ttt | t |
| Pro<br>370 | Pro | Cys | Pro | Ala | Gly<br>375 | Trp | Ile | Ser | Leu | Trp<br>380 | Lys | Gly | Phe | S |
| atc | atg | ttc | aca | agt | gct | ggt | tcg | gag | ggt | gct | ggg | caa | gca | c |
| Ile<br>385 | Met | Phe | Thr | Ser | Ala<br>390 | Gly | Ser | Glu | Gly | Ala<br>395 | Gly | Gln | Ala | L |
| tcc | ccc | ggc | tcc | tgc | ctg | gaa | gaa | ttc | cga | gcc | agt | cca | ttt | a |
| Ser<br>405 | Pro | Gly | Ser | Cys | Leu<br>410 | Glu | Glu | Phe | Arg | Ala<br>415 | Ser | Pro | Phe | I |
| tgt | cac | gga | aga | gga | aca | tgt | aac | tac | tat | tca | aac | tcc | tac | a |
| Cys<br>420 | His | Gly | Arg | Gly | Thr<br>425 | Cys | Asn | Tyr | Tyr | Ser<br>430 | Asn | Ser | Tyr | S |
| tgg | ttg | gct | tca | tta | gac | ccc | aaa | aga | atg | ttc | aga | aaa | cct | a |
| Trp<br>435 | Leu | Ala | Ser | Leu | Asp<br>440 | Pro | Lys | Arg | Met | Phe<br>445 | Arg | Lys | Pro | I |
| tca | act | gtg | aaa | gct | ggg | gag | tta | gaa | aac | ata | ata | agt | cgc | t |
| Ser<br>450 | Thr | Val | Lys | Ala | Gly<br>455 | Glu | Leu | Glu | Asn | Ile<br>460 | Ile | Ser | Arg | C |
| gtg | tgc | atg | aag | atg | aga | cca | tga |  | 1416 |  |  |  |  |  |
| Val<br>465 | Cys | Met | Lys | Met | Arg<br>470 | Pro | End |  |  |  |  |  |  |  |

(2) INFORMATION FOR SEQ ID NO: 2:

(i) SEQUENCE CHARACTERISTICS:
(A) LENGTH: 657 base pairs
(B) TYPE: Nucleic acid
(C) STRANDEDNESS: Double
(D) TOPOLOGY: Linear (ii) MOLECULE TYPE: cDNA to mRNA (iii) HYPOTHETICAL: No (iv) ANTI-SENSE: No (vi) ORIGINAL SOURCE:
(A) ORGANISM: Human
(B) STRAIN: Not applicable
(C) INDIVIDUAL ISOLATE: Not known
(D) DEVELOPMENTAL STAGE: Adult
(G) CELL TYPE: Whole kidney (vii) IMMEDIATE SOURCE:
(A) LIBRARY: Whole kidney cDNA
(B) CLONE: KMC27

(viii) POSITION IN GENOME:
(A) CHROMOSOME/SEGMENT: Not known (x) PUBLICATION INFORMATION: None (xi) SEQUENCE DESCRIPTION: SEQ ID NO: 2:

|  |  |  |  |  |  |  |  |  |  |  |  |  |
|---|---|---|---|---|---|---|---|---|---|---|---|---|
| CAA | ACC | ACA | GCA | ATT | CCT | TCA | TGT | CCA | GAG | GGG | ACA | GTG | CCA | C |
| Gln<br>5 | Thr | Thr | Ala | Ile | Pro<br>10 | Ser | Cys | Pro | Glu | Gly<br>15 | Thr | Val | Pro | L |

-continued

```
            AGT GGG TTT TCT TTT CTT TTT GTA CAA GGA AAT CAA CGA GCC C
            Ser Gly Phe Ser Phe Leu Phe Val Gln Gly Asn Gln Arg Ala H
            20              25                      30
            CAA GAC CTT GGA ACT CTT GGC AGC TGC CTG CAG CGA TTT ACC A
            Gln Asp Leu Gly Thr Leu Gly Ser Cys Leu Gln Arg Phe Thr T
            35              40                      45
            CCA TTC TTA TTC TGC AAT GTC AAT GAT GTA TGT AAT TTT GCA T
            Pro Phe Leu Phe Cys Asn Val Asn Asp Val Cys Asn Phe Ala S
            50              55                      60
            AAT GAT TAT TCA TAC TGG CTG TCA ACA CCA GCT CTG ATG CCA A
            Asn Asp Tyr Ser Tyr Trp Leu Ser Thr Pro Ala Leu Met Pro M
            65              70                      75
            ATG GCT CCC ATT ACT GGC AGA GCC CTT GAG CCT TAT ATA AGC A
            Met Ala Pro Ile Thr Gly Arg Ala Leu Glu Pro Tyr Ile Ser A
            85              90                      95
            ACT GTT TGT GAA GGT CCT GCG ATC GCC ATA GCC GTT CAC AGC C
            Thr Val Cys Glu Gly Pro Ala Ile Ala Ile Ala Val His Ser G
            100             105                     110
            ACT GAC ATT CCT CCA TGT CCT CAC GGC TGG ATT TCT CTC TGG A
            Thr Asp Ile Pro Pro Cys Pro His Gly Trp Ile Ser Leu Trp L
            115             120                     125
            TTT TCA TTC ATC ATG TTC ACA AGT GCA GGT TCT GAG GGC GCC G
            Phe Ser Phe Ile Met Phe Thr Ser Ala Gly Ser Glu Gly Ala G
            130             135                     140
            GCA CTG GCC TCC CCC GGC TCC TGC CTG GAA GAA TTC CGA GCC A
            Ala Leu Ala Ser Pro Gly Ser Cys Leu Glu Glu Phe Arg Ala S
            145             150                     155
            TTT CTA GAA TGT CAT GGA AGA GGA ACG TGC AAC TAC TAT TCA A
            Phe Leu Glu Cys His Gly Arg Gly Thr Cys Asn Tyr Tyr Ser A
            165             170                     175
            TAC AGT TTC TGG CTG GCT TCA TTA AAC CCA GAA AGA ATG TTC A
            Tyr Ser Phe Trp Leu Ala Ser Leu Asn Pro Glu Arg Met Phe A
            180             185                     190
            CCT ATT CCA TCA ACT GTG AAA GCT GGG GAA TTA GAA AAA ATA A
            Pro Ile Pro Ser Thr Val Lys Ala Gly Glu Leu Glu Lys Ile I
            195             200                     205
            CGC TGT CAG GTG TGC ATG AAG AAA AGA CAC TGA 657
            Arg Cys Gln Val Cys Met Lys Lys Arg His End
            210             215
```

(2) INFORMATION FOR SEQ ID NO: 3:

(i) SEQUENCE CHARACTERISTICS:
        (A) LENGTH: 12 amino acid residues
        (B) TYPE: Amino acid
        (D) TOPOLOGY: Linear (ii) MOLECULE TYPE: cDNA to mRNA
        (A) DESCRIPTION: Synthetic peptide corresponding to the deduc
            amino acid sequence of the carboxy terminal 12 amino acid (v) FRAGMENT TYPE: C-terminal fragment (vi) ORIGINAL SOURCE:
        (A) ORGANISM: Human
        (C) INDIVIDUAL ISOLATE: Unknown
        (D) DEVELOPMENTAL STAGE: Unknown
        (G) CELL TYPE: Whole human kidney (x) PUBLICATION INFORMATION: None (xi) SEQUENCE DESCRIPTION: SEQ ID NO: 3:
        Ile Ser Arg Cys Gln Val Cys Met Lys Lys Arg His
        5                  10

(2) INFORMATION FOR SEQ ID NO: 4:

(i) SEQUENCE CHARACTERISTICS:
        (A) LENGTH: 17 nucleotides
        (B) TYPE: Nucleic acid
        (C) STRANDEDNESS: Single
        (D) TOPOLOGY: Linear (ii) MOLECULE TYPE: cDNA to mRNA (iii) HYPOTHETICAL: No (iv) ANTI-SENSE: No (vi) ORIGINAL SOURCE:
        (A) ORGANISM: Human
        (B) STRAIN: Not applicable ( C ) INDIVIDUAL ISOLATE: Not known
              ( D ) DEVELOPMENTAL STAGE: Adult
              ( G ) CELL TYPE: Whole kidney ( v i i ) IMMEDIATE SOURCE:
              ( A ) LIBRARY: Whole kidney cDNA
              ( B ) CLONE: KMC27

( v i i i ) POSITION IN GENOME:
              ( A ) CHROMOSOME/SEGMENT: Not known ( x ) PUBLICATION INFORMATION: None ( x i ) SEQUENCE DESCRIPTION: SEQ ID NO: 4:
              AAGCCNGGNG AYACAGG                    17

( 2 ) INFORMATION FOR SEQ ID NO: 5:

( i ) SEQUENCE CHARACTERISTICS:
              ( A ) LENGTH: 17 nucleotides
              ( B ) TYPE: Nucleic acid
              ( C ) STRANDEDNESS: Single
              ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
              ( A ) ORGANISM: Human
              ( B ) STRAIN: Not applicable
              ( C ) INDIVIDUAL ISOLATE: Not known
              ( D ) DEVELOPMENTAL STAGE: Adult
              ( G ) CELL TYPE: Whole kidney ( v i i ) IMMEDIATE SOURCE:
              ( A ) LIBRARY: Whole kidney cDNA
              ( B ) CLONE: KMC27

( v i i i ) POSITION IN GENOME:
              ( A ) CHROMOSOME/SEGMENT: Not known ( x ) PUBLICATION INFORMATION: None ( x i ) SEQUENCE DESCRIPTION: SEQ ID NO: 5:
              AAGCCNGGNG AYACCGG                    17

( 2 ) INFORMATION FOR SEQ ID NO: 6:

( i ) SEQUENCE CHARACTERISTICS:
              ( A ) LENGTH: 17 nucleotides
              ( B ) TYPE: Nucleic acid
              ( C ) STRANDEDNESS: Single
              ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
              ( A ) ORGANISM: Human
              ( B ) STRAIN: Not applicable
              ( C ) INDIVIDUAL ISOLATE: Not known
              ( D ) DEVELOPMENTAL STAGE: Adult
              ( G ) CELL TYPE: Whole kidney ( v i i ) IMMEDIATE SOURCE:
              ( A ) LIBRARY: Whole kidney cDNA
              ( B ) CLONE: KMC27

( v i i i ) POSITION IN GENOME:
              ( A ) CHROMOSOME/SEGMENT: Not known ( x ) PUBLICATION INFORMATION: None ( x i ) SEQUENCE DESCRIPTION: SEQ ID NO: 6:
              AAGCCNGGNG AYACGGG                    17

( 2 ) INFORMATION FOR SEQ ID NO: 7:

( i ) SEQUENCE CHARACTERISTICS:
        ( A ) LENGTH: 17 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Human
        ( B ) STRAIN: Not applicable
        ( C ) INDIVIDUAL ISOLATE: Not known
        ( D ) DEVELOPMENTAL STAGE: Adult
        ( G ) CELL TYPE: Whole kidney ( v i i ) IMMEDIATE SOURCE:
        ( A ) LIBRARY: Whole kidney cDNA
        ( B ) CLONE: KMC27

( v i i i ) POSITION IN GENOME:
        ( A ) CHROMOSOME/SEGMENT: Not known ( x ) PUBLICATION INFORMATION: None ( x i ) SEQUENCE DESCRIPTION: SEQ ID NO: 7:
        AAGCCNGGNG AYACTGG        17

( 2 ) INFORMATION FOR SEQ ID NO: 8:

( i ) SEQUENCE CHARACTERISTICS:
        ( A ) LENGTH: 20 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Human
        ( B ) STRAIN: Not applicable
        ( C ) INDIVIDUAL ISOLATE: Not known
        ( D ) DEVELOPMENTAL STAGE: Adult
        ( G ) CELL TYPE: Whole kidney ( v i i ) IMMEDIATE SOURCE:
        ( A ) LIBRARY: Whole kidney cDNA
        ( B ) CLONE: KMC27

( v i i i ) POSITION IN GENOME:
        ( A ) CHROMOSOME/SEGMENT: Not known ( x ) PUBLICATION INFORMATION: None ( x i ) SEQUENCE DESCRIPTION: SEQ ID NO: 8:
        TARTGYCTNG TRAANACAAA        20

( 2 ) INFORMATION FOR SEQ ID NO: 9:

( i ) SEQUENCE CHARACTERISTICS:
        ( A ) LENGTH: 20 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Human (B) STRAIN: Not applicable
            (C) INDIVIDUAL ISOLATE: Not known
            (D) DEVELOPMENTAL STAGE: Adult
            (G) CELL TYPE: Whole kidney (vii) IMMEDIATE SOURCE:
            (A) LIBRARY: Whole kidney cDNA
            (B) CLONE: KMC27

(viii) POSITION IN GENOME:
            (A) CHROMOSOME/SEGMENT: Not known (x) PUBLICATION INFORMATION: None (xi) SEQUENCE DESCRIPTION: SEQ ID NO: 9:
                TARTGYCTNG TRAANACGAA          20

(2) INFORMATION FOR SEQ ID NO: 10:

(i) SEQUENCE CHARACTERISTICS:
            (A) LENGTH: 20 nucleotides
            (B) TYPE: Nucleic acid
            (C) STRANDEDNESS: Single
            (D) TOPOLOGY: Linear (ii) MOLECULE TYPE: cDNA to mRNA (iii) HYPOTHETICAL: No (iv) ANTI-SENSE: No (vi) ORIGINAL SOURCE:
            (A) ORGANISM: Human
            (B) STRAIN: Not applicable
            (C) INDIVIDUAL ISOLATE: Not known
            (D) DEVELOPMENTAL STAGE: Adult
            (G) CELL TYPE: Whole kidney (vii) IMMEDIATE SOURCE:
            (A) LIBRARY: Whole kidney cDNA
            (B) CLONE: KMC27

(viii) POSITION IN GENOME:
            (A) CHROMOSOME/SEGMENT: Not known (x) PUBLICATION INFORMATION: None (xi) SEQUENCE DESCRIPTION: SEQ ID NO: 10:
                TARTGNCGNG TRAANACAAA          20

(2) INFORMATION FOR SEQ ID NO: 11:

(i) SEQUENCE CHARACTERISTICS:
            (A) LENGTH: 20 nucleotides
            (B) TYPE: Nucleic acid
            (C) STRANDEDNESS: Single
            (D) TOPOLOGY: Linear (ii) MOLECULE TYPE: cDNA to mRNA (iii) HYPOTHETICAL: No (iv) ANTI-SENSE: No (vi) ORIGINAL SOURCE:
            (A) ORGANISM: Human
            (B) STRAIN: Not applicable
            (C) INDIVIDUAL ISOLATE: Not known
            (D) DEVELOPMENTAL STAGE: Adult
            (G) CELL TYPE: Whole kidney (vii) IMMEDIATE SOURCE:
            (A) LIBRARY: Whole kidney cDNA
            (B) CLONE: KMC27

(viii) POSITION IN GENOME:
            (A) CHROMOSOME/SEGMENT: Not known (x) PUBLICATION INFORMATION: None (xi) SEQUENCE DESCRIPTION: SEQ ID NO: 11:
                TARTGNCGNG TRAANACGAA          20

( 2 ) INFORMATION FOR SEQ ID NO: 12:

( i ) SEQUENCE CHARACTERISTICS:
        ( A ) LENGTH: 17 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Human
        ( B ) STRAIN: Not applicable
        ( C ) INDIVIDUAL ISOLATE: Not known
        ( D ) DEVELOPMENTAL STAGE: Adult
        ( G ) CELL TYPE: Whole kidney ( v i i ) IMMEDIATE SOURCE:
        ( A ) LIBRARY: Whole kidney cDNA
        ( B ) CLONE: KMC27

( v i i i ) POSITION IN GENOME:
        ( A ) CHROMOSOME/SEGMENT: Not known ( x ) PUBLICATION INFORMATION: None ( x i ) SEQUENCE DESCRIPTION: SEQ ID NO: 12:
        GCNGGNCGNG TNATGCG      17

( 2 ) INFORMATION FOR SEQ ID NO: 13:

( i ) SEQUENCE CHARACTERISTICS:
        ( A ) LENGTH: 17 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Human
        ( B ) STRAIN: Not applicable
        ( C ) INDIVIDUAL ISOLATE: Not known
        ( D ) DEVELOPMENTAL STAGE: Adult
        ( G ) CELL TYPE: Whole kidney ( v i i ) IMMEDIATE SOURCE:
        ( A ) LIBRARY: Whole kidney cDNA
        ( B ) CLONE: KMC27

( v i i i ) POSITION IN GENOME:
        ( A ) CHROMOSOME/SEGMENT: Not known ( x ) PUBLICATION INFORMATION: None ( x i ) SEQUENCE DESCRIPTION: SEQ ID NO: 13:
        GCNGGNCGNG TNATGAG      17

( 2 ) INFORMATION FOR SEQ ID NO: 14:

( i ) SEQUENCE CHARACTERISTICS:
        ( A ) LENGTH: 19 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:

(A) ORGANISM: Human
(B) STRAIN: Not applicable
(C) INDIVIDUAL ISOLATE: Not known
(D) DEVELOPMENTAL STAGE: Adult
(G) CELL TYPE: Whole kidney (vii) IMMEDIATE SOURCE:
(A) LIBRARY: Whole kidney cDNA
(B) CLONE: KMC27

(viii) POSITION IN GENOME:
(A) CHROMOSOME/SEGMENT: Not known (x) PUBLICATION INFORMATION: None (xi) SEQUENCE DESCRIPTION: SEQ ID NO: 14:
GTNTTYACNA GRCAYTATC        19

(2) INFORMATION FOR SEQ ID NO: 15:

(i) SEQUENCE CHARACTERISTICS:
(A) LENGTH: 22 nucleotides
(B) TYPE: Nucleic acid
(C) STRANDEDNESS: Single
(D) TOPOLOGY: Linear (ii) MOLECULE TYPE: cDNA to mRNA (iii) HYPOTHETICAL: No (iv) ANTI-SENSE: No (vi) ORIGINAL SOURCE:
(A) ORGANISM: Human
(B) STRAIN: Not applicable
(C) INDIVIDUAL ISOLATE: Not known
(D) DEVELOPMENTAL STAGE: Adult
(G) CELL TYPE: Whole kidney (vii) IMMEDIATE SOURCE:
(A) LIBRARY: Whole kidney cDNA
(B) CLONE: KMC27

(viii) POSITION IN GENOME:
(A) CHROMOSOME/SEGMENT: Not known (x) PUBLICATION INFORMATION: None (xi) SEQUENCE DESCRIPTION: SEQ ID NO: 15:
CCAGGMGAYA CHGGNCCHCC AG        22

(2) INFORMATION FOR SEQ ID NO: 16:

(i) SEQUENCE CHARACTERISTICS:
(A) LENGTH: 21 nucleotides
(B) TYPE: Nucleic acid
(C) STRANDEDNESS: Single
(D) TOPOLOGY: Linear (ii) MOLECULE TYPE: cDNA to mRNA (iii) HYPOTHETICAL: No (iv) ANTI-SENSE: No (vi) ORIGINAL SOURCE:
(A) ORGANISM: Human
(B) STRAIN: Not applicable
(C) INDIVIDUAL ISOLATE: Not known
(D) DEVELOPMENTAL STAGE: Adult
(G) CELL TYPE: Whole kidney (vii) IMMEDIATE SOURCE:
(A) LIBRARY: Whole kidney cDNA
(B) CLONE: KMC27

(viii) POSITION IN GENOME:
(A) CHROMOSOME/SEGMENT: Not known (x) PUBLICATION INFORMATION: None (xi) SEQUENCE DESCRIPTION: SEQ ID NO: 16:

CAGGAAGGGC ATKGTGCTGA A                    21

( 2 ) INFORMATION FOR SEQ ID NO: 17:

( i ) SEQUENCE CHARACTERISTICS:
        ( A ) LENGTH: 20 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Human
        ( B ) STRAIN: Not applicable
        ( C ) INDIVIDUAL ISOLATE: Not known
        ( D ) DEVELOPMENTAL STAGE: Adult
        ( G ) CELL TYPE: Whole kidney ( v i i ) IMMEDIATE SOURCE:
        ( A ) LIBRARY: Whole kidney cDNA
        ( B ) CLONE: KMC27

( v i i i ) POSITION IN GENOME:
        ( A ) CHROMOSOME/SEGMENT: Not known ( x ) PUBLICATION INFORMATION: None ( x i ) SEQUENCE DESCRIPTION: SEQ ID NO: 17:
        GGSGCCTCAC ACACAGMACA                    20

( 2 ) INFORMATION FOR SEQ ID NO: 18:

( i ) SEQUENCE CHARACTERISTICS:
        ( A ) LENGTH: 20 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
        ( A ) ORGANISM: Human
        ( B ) STRAIN: Not applicable
        ( C ) INDIVIDUAL ISOLATE: Not known
        ( D ) DEVELOPMENTAL STAGE: Adult
        ( G ) CELL TYPE: Whole kidney ( v i i ) IMMEDIATE SOURCE:
        ( A ) LIBRARY: Whole kidney cDNA
        ( B ) CLONE: KMC27

( v i i i ) POSITION IN GENOME:
        ( A ) CHROMOSOME/SEGMENT: Not known ( x ) PUBLICATION INFORMATION: None ( x i ) SEQUENCE DESCRIPTION: SEQ ID NO: 18:
        TTGCAG W ACA GGAAGGGCAT                    20

( 2 ) INFORMATION FOR SEQ ID NO: 19:

( i ) SEQUENCE CHARACTERISTICS:
        ( A ) LENGTH: 17 nucleotides
        ( B ) TYPE: Nucleic acid
        ( C ) STRANDEDNESS: Single
        ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
    ( A ) ORGANISM: Human
    ( B ) STRAIN: Not applicable
    ( C ) INDIVIDUAL ISOLATE: Not known
    ( D ) DEVELOPMENTAL STAGE: Adult
    ( G ) CELL TYPE: Whole kidney ( v i i ) IMMEDIATE SOURCE:
    ( A ) LIBRARY: Whole kidney cDNA
    ( B ) CLONE: KMC27

( v i i i ) POSITION IN GENOME:
    ( A ) CHROMOSOME/SEGMENT: Not known ( x ) PUBLICATION INFORMATION: None ( x i ) SEQUENCE DESCRIPTION: SEQ ID NO: 19:
    TTGCAG W ACA GGAAGGG    17

( 2 ) INFORMATION FOR SEQ ID NO: 20:

( i ) SEQUENCE CHARACTERISTICS:
    ( A ) LENGTH: 23 nucleotides
    ( B ) TYPE: Nucleic acid
    ( C ) STRANDEDNESS: Single
    ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
    ( A ) ORGANISM: Human
    ( B ) STRAIN: Not applicable
    ( C ) INDIVIDUAL ISOLATE: Not known
    ( D ) DEVELOPMENTAL STAGE: Adult
    ( G ) CELL TYPE: Whole kidney ( v i i ) IMMEDIATE SOURCE:
    ( A ) LIBRARY: Whole kidney cDNA
    ( B ) CLONE: KMC27

( v i i i ) POSITION IN GENOME:
    ( A ) CHROMOSOME/SEGMENT: Not known ( x ) PUBLICATION INFORMATION: None ( x i ) SEQUENCE DESCRIPTION: SEQ ID NO: 20:
    CCCGATGGGT TGCCAGGATC CAT    23

( 2 ) INFORMATION FOR SEQ ID NO: 21:

( i ) SEQUENCE CHARACTERISTICS:
    ( A ) LENGTH: 20 nucleotides
    ( B ) TYPE: Nucleic acid
    ( C ) STRANDEDNESS: Single
    ( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
    ( A ) ORGANISM: Human
    ( B ) STRAIN: Not applicable
    ( C ) INDIVIDUAL ISOLATE: Not known
    ( D ) DEVELOPMENTAL STAGE: Adult
    ( G ) CELL TYPE: Whole kidney ( v i i ) IMMEDIATE SOURCE:
    ( A ) LIBRARY: Whole kidney cDNA
    ( B ) CLONE: KMC27

( v i i i ) POSITION IN GENOME:
    ( A ) CHROMOSOME/SEGMENT: Not known ( x ) PUBLICATION INFORMATION: None ( x i ) SEQUENCE DESCRIPTION: SEQ ID NO: 21:
  TGACTATGCC TGGTCACAAG    20

( 2 ) INFORMATION FOR SEQ ID NO: 22:

( i ) SEQUENCE CHARACTERISTICS:
    ( A ) LENGTH: 6 amino acid residues
    ( B ) TYPE: Amino acid
    ( D ) TOPOLOGY: Linear ( i i ) MOLECULE TYPE: cDNA to mRNA
    ( A ) DESCRIPTION: Hypothetical peptide corresponding to six
      deduced amino acids of SEQ ID NO 1

( v i ) ORIGINAL SOURCE:
    ( A ) ORGANISM: Human
    ( C ) INDIVIDUAL ISOLATE: Unknown
    ( D ) DEVELOPMENTAL STAGE: Unknown
    ( G ) CELL TYPE: Whole human kidney ( x ) PUBLICATION INFORMATION: None ( x i ) SEQUENCE DESCRIPTION: SEQ ID NO: 22:
      Lys Pro Gly Asp Thr Gly
      5

( 2 ) INFORMATION FOR SEQ ID NO: 23:

( i ) SEQUENCE CHARACTERISTICS:
    ( A ) LENGTH: 7 amino acid residues
    ( B ) TYPE: Amino acid
    ( D ) TOPOLOGY: Linear ( i i ) MOLECULE TYPE: cDNA to mRNA
    ( A ) DESCRIPTION: Hypothetical peptide corresponding to six
      deduced amino acids of SEQ ID NO 1

( v i ) ORIGINAL SOURCE:
    ( A ) ORGANISM: Human
    ( C ) INDIVIDUAL ISOLATE: Unknown
    ( D ) DEVELOPMENTAL STAGE: Unknown
    ( G ) CELL TYPE: Whole human kidney ( x ) PUBLICATION INFORMATION: None ( x i ) SEQUENCE DESCRIPTION: SEQ ID NO: 23:
      Tyr His Arg Phe Ala Val Phe
      5

Figure 8A:
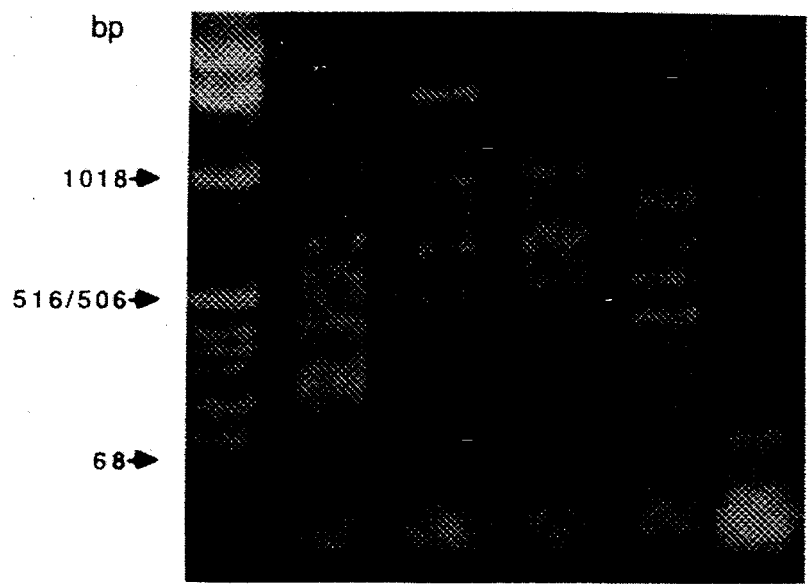

FIG. 8A depict blots concerning PCR reaction products obtained using a bovine genomic template. The primers used are indicated below each lane. F9* and R9* are primers complementary to corresponding regions of human α1(IV). Arrows mark the positions of the 1018 and 516/506 bp marker fragments (lane M) and the expected position of a 68 bp fragment. PCR conditions: denature 94° C.; 1 min: anneal 60° C.; 15 secs: extend 72° C.; 30 secs (30 cycles).

Figure 8B:
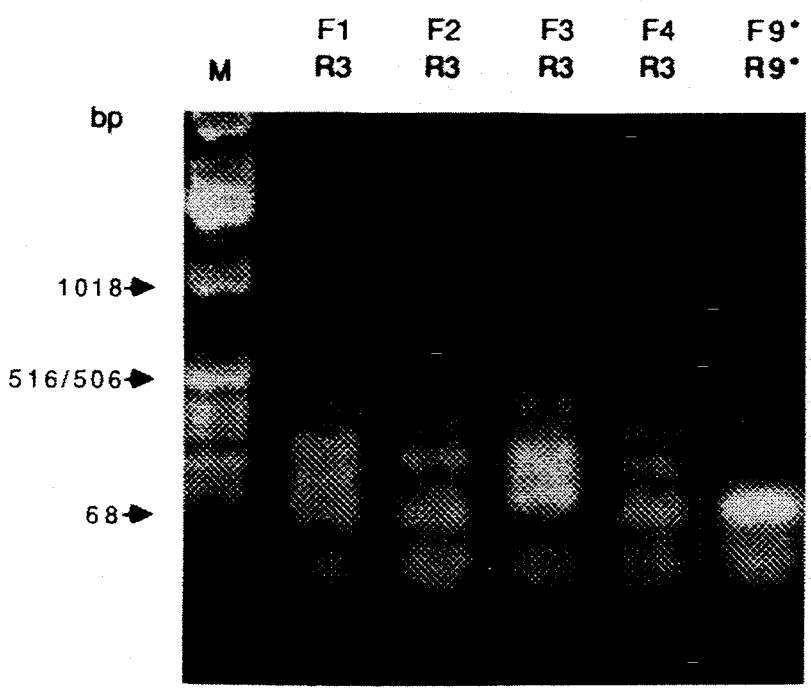

FIG. 8B depicts blots concerning reactions identical to those in FIG. 8 a except for the PCR cycling profile: denature 94° C.; 1 min, anneal 68° C.; 30 secs (2 cycles): denature 94° C.; 1 min, anneal 66° C.; 30 secs (2 cycles): denature 94° C.; 1 min, anneal 64° C.; 30 secs (2 cycles): denature 94° C.; 1 min, anneal 58° C. for 28 cycles.

Figure 9:
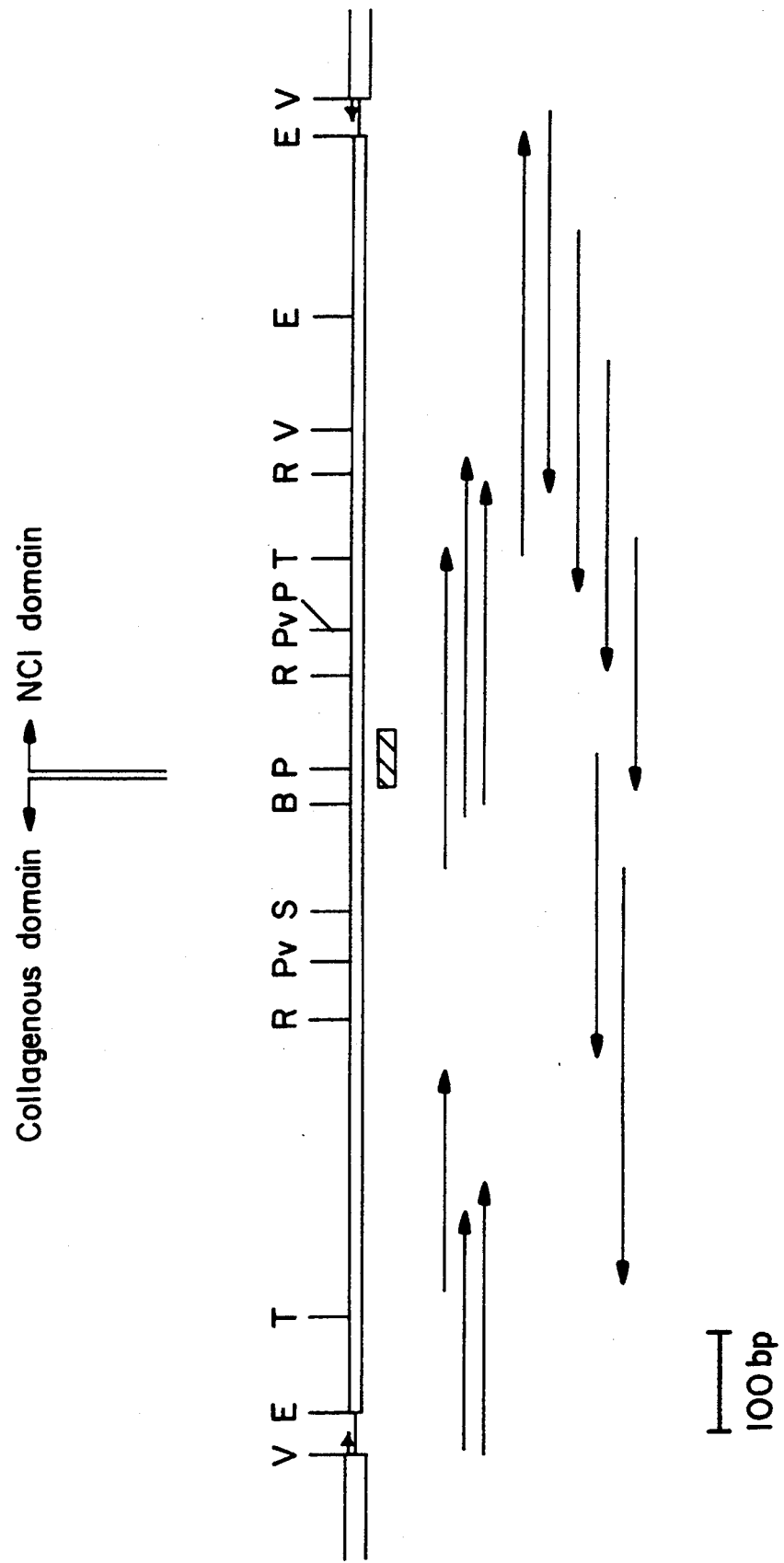

FIG. 9 is a restriction map and sequencing strategy for KEMC15. cDNA from KEMC15 is represented by the solid thick line, pBluescript by the open-ended hollow bars and λgt11 by the solid thin line. Solid arrows indicate the length and orientation of sequence analysis. Open arrows (→) show the position of the λgt11 primers used to amplify the cDNA library insert. The position of the probe KEM68 is shown by a hatched box. Restriction sites for BamHI (B), EcoRI (E), EcoRV(V), PstI,(P), PvuII(Pv), RsaI(R), SmaI(S) and TagI(T) are indicated.

DETAILED DESCRIPTION OF THE INVENTION

The present invention concerns a novel type IV collagen, α3(IV) isolated from human and bovine basement membranes. The noncollagenous (NC1) domain of α3(IV) is of particular interest as it appears to be the component of the basement membrane which reacts maximally with the Goodpasture antibody. The cloning and sequencing of a cDNA encoding 218 residues of the NC1 domain of the human α3(IV) chain, COL4A3 is described herein and will permit further study of the nature of the Goodpasture epitope. It will allow in vitro synthesis of the epitope, for use in diagnostic screening and for adsorption of pathogenic antibody for treatment of the disorder. Of further interest is the possible role of abnormalities of the α3(IV) chain in Alport syndrome, as suggested by immunological and chemical data. To determine whether α3(IV) may be mutated in Alport syndrome, applicants localized the COL4A3 gene, by somatic cell hybrid analysis and in situ hybridization of metaphase to chromosome 2. Mutations in α3(IV) cannot therefore be responsible for the vast majority of cases of Alport syndrome, which have been shown to be X-linked. One explanation for the immunochemical data is that mutations of the α5(IV) chain, which has been localized to Xq22 and found to be mutated in at least 3 kindreds with Alport syndrome, lead to failure to incorporate the α3(IV) chains into the multimeric structure of glomerular basement membrane.

It remains to be determined whether AS (Alport syndrome) mutations are confined to the α5(IV) chain or whether they also involve other type IV collagens as suggested by the immunochemical data. Applicants therefore cloned the gene encoding the α3(IV) chain as a step towards characterizing the Goodpasture antigen and determining the possible role of mutations of α3-(IV) in Alport syndrome. Using the polymerase chain reaction (PCR) with primers derived from each end of the known 27 amino acid residue bovine α3(IV) protein sequence, a 68 bp bovine genomic fragment was amplified (Morrison et al. 1991). This fragment was then used to probe a bovine lens cDNA library and a 1.5 kb partial cDNA clone obtained. This encodes 238 residues of the triple helical collagenous domain and all 233 residues of the NC1 domain of the α3(IV) chain. As described here, this bovine cDNA clone was used to screen a human kidney cDNA library and a 2.7 kb human cDNA clone obtained. This clone encodes 218 residues of the NC1 domain and a portion of the 3' untranslated region of the human α3(IV) chain. Applicants have mapped this gene using somatic cell hybrids and by in situ hybridization. These techniques localize the COL4A3 gene to chromosome 2. Clearly, as the majority of cases of Alport syndrome are X-linked, mutations in COL4A3 cannot be responsible for the disorder in these patients. A mechanism whereby mutations in COL4A5 could lead to a failure to incorporate the α3(IV) chain into heterotrimers and hence into the 3-dimensional structure of basement membrane, is proposed.

The NC1 domains of type IV collagen can be excised from the basement membrane by cleavage with bacterial collagenase. The excised domains exist as hexamers, which can be separated by denaturing polyacrylamide gel electrophoresis to yield a number of monomeric and dimeric species (Butkowski et al. 1985). Maximal reactivity to serum containing Goodpasture antibody resides in the subunit Mr=28,300, designated M28+++ in human tissue or M2* in bovine tissue (Butkowski et al. 1985; Wieslander et al. 1985). This subunit has been taken to be the NC1 domain of a novel type IV collagen, α3(IV), as it has many physical features in common with the abundant α1(IV) and α2(IV) chains, yet is clearly distinct from them (Hudson et al. 1989).

Short portions of the junctional region between the collagenous and NC1 domain of the α3(IV) chain have been sequenced in both human and bovine tissue (Saus et al. 1988; Butkowski et al. 1990). Using a PCR based strategy, with primers derived from the short bovine α3(IV) peptide sequence, applicants have cloned partial cDNAs encoding the NC1 domain of the bovine α3(IV) chain (Morrison et al. 1991) and used the bovine/human homology to clone and localize the 3' end of the human α3(IV) chain.

The amino acid sequence of α3(IV) derived from the clone KMC27 will allow further investigation of the nature of the Goodpasture epitope. It will also be of value in the design of improved assays for the specific Goodpasture antibody. At present, assays for Goodpasture syndrome rely on a crude collagenase digest of GBM. This yields occasional false positive results, as patients with other forms of nephritis develop circulating antibodies to a variety of basement membrane components, secondary to other disease processes. For example, patients with IgA nephropathy develop immune complexes containing fibronectin and IgA that bind to the triple helical domain of type IV collagen (Cederholm et al. 1988); several patients with poststreptococcal glomerulonephritis have circulating antibodies against the 7S domain of type IV collagen and heparan sulphate proteoglycan (Fillit et al. 1985; Kefalides et al. 1986). The sequence data given here will be used to design synthetic peptides that will specifically detect anticollagen—α3(IV). Such peptides can also be used for adsorption of the pathogenic antibody, offering a novel treatment option for Goodpasture syndrome.

Attention has also been focussed on the possible role of mutations of the α3(IV) chain in Alport syndrome. Several investigators have found that binding of Goodpasture antibody to GBM is frequently absent in patients with this disease, as determined by immunofluorescence of GBM tissue sections (Olsen et al. 1980; Jenis et al. 1981; Jeraj et al. 1983; Kashtan et al. 1986). Absent or reduced binding of a monoclonal antibody directed towards the Goodpasture antigen has also been shown in renal biopsies from 10 Alport patients (Savage et al. 1986). In addition, immunochemical and chemical evidence for the absence of the collagenase solubilized human Goodpasture antigen, M28+++, in the GBM of 3 patients with X-linked Alport syndrome, has been obtained (Kleppel et al. 1987). Others however, report a partial, rather than complete loss of the Goodpasture antigen in GBM sections from affected individuals (McCoy et al. 1982).

There is evidence, however, that suggests that an abnormality of the α3(IV) chain may not be the primary defect in Alport syndrome. Recently the gene encoding a further novel collagen chain, α5(IV), has been cloned, mapped to the Xq22 region and found to be mutated in at least 3 of 18 kindreds with this heterogeneous disorder (Hostikka et al. 1990; Myers et al. 1990). Several investigators have reported Alport patients who, on transplantation, develop antibodies to a 26kD protein, rather than to the 28kD protein expected if such antibodies were targeted to the NC1 domain of the α3(IV) chain (Kashtan et al. 1986; Savage et al. 1989). The estimated size of the α5(IV) NC1 domain is 26kD, and may well represent the target of the the post-transplantation antibodies. Kleppel et al. (1989) have shown that both a post-transplantation antibody which recognizes the 26kD protein, and an antibody to the 28kD protein show an identical binding pattern to the glomerular basement membrane of a female heterozygote with Alport syndrome, consistent with random inactivation of the X chromosome.

To understand the molecular pathology of Alport syndrome, one must explain why α3(IV) is not found in the GBM of patients with the X-linked form of the disease, which at least in some cases is produced by an α5(IV) mutation. One hypothesis was that the α3(IV) and α5(IV) chains are both encoded on the X chromosome, perhaps in a head-to-head arrangement such as that observed for the α1(IV) and α2(IV) genes on chromosome 13 (Poschl et al. 1988)). As we have shown here, the gene encoding the NC1 domain of α3(IV) maps to the 2xx region. Therefore, mutations in α3(IV) cannot be responsible for the majority of cases of Alport syndrome, which are clearly X-linked (Atkins et al. 1988; Brunner et al. 1988; Flinter et al. 1988). Whether mutations in the α3(IV) chain are responsible for those cases of Alport syndrome which are said to be autosomal remains to be determined.

How then can the immunological and chemical data implicating an abnormality in the α3(IV) chain in patients with X-linked Alport syndrome be explained? One hypothesis is that, in the presence of certain but not all mutations of α5(IV), the α3(IV) chain is not stably incorporated into heterotrimers, and thence into the basement membrane. If so, one would expect that a subset of α5(IV) mutations reduce or abolish the incorporation of the α3(IV) chain (and thus reactivity to the Goodpasture antibody), while others do not affect α3-(IV) chain incorporation, and thus reactivity to the Goodpasture antibody is preserved. If the defect is one of stable incorporation of α3(IV) chains into heterotrimers in the presence of α5(IV) mutations, rather than an abnormality of the α3(IV) chain per se, then transcription of COL4A3 should be normal in the kidneys of individuals with X-linked Alport syndrome.

Maximal reactivity to serum containing Goodpasture antibody resides in the subunit Mr=28,300, designated M2* in bovine tissue and a similarly sized subunit, M28+++, in human tissue (Butkowski et al, (1985), *J. Biol. Chem.*, 260, 3739-3747; Wieslander et al, (1985), *J. Biol. Chem.*, 260, 8564-8570).

M2* has been isolated from bovine GBM (glomerular basement molecule) and LBM (lens basement molecule), and a short portion of the M2* peptide from LBM has been sequenced (Saus et al, (1988) *J. Biol. Chem.*, 263, 13374-13380). M2* has been taken to be the NC1 domain of a novel type (IV) collagen, α3(IV), as it is clearly distinct from the abundant α1(IV) and α2(IV) chains, and yet has many features in common with them. It exists in monomeric and dimeric forms, has a similar molecular weight and, based on immunoprecipitation studies, is an integral component of the NC1 (noncollagenous) hexamer of collagen IV. The short amino acid sequence of α3(IV) available from the collagenous/NC1 junction revealed Gly-Xaa-Yaa triplets at the amino terminus end together with 13 residues of the NC1 domain, 8 of which were identical to the residues in the same region of the α1(IV) chain.

Disclosed herein is a PCR strategy used to clone a portion of the bovine α3(IV) gene. Degenerate oligonucleotide primers complementary to each end of the short portion of the known M2* peptide sequence were used in the PCR (polymerase chain reaction) to amplify a 68 base pair bovine genomic fragment. PCR cycles were performed using a high (68° C.) annealing temperature at first, with a stepwise reduction (1° or 2° C.)in annealing temperature in subsequent cycles. In this way, although the amount of primer bound to the template during the initial amplification cycles is small, exactly complementary primer/template interactions represent a higher proportion of the total primer/template interactions than that which occurs at lower annealing temperatures. Therefore amplification of the desired target is favored. The small 68 base pair fragment thus obtained, KEM68, was then used to probe a bovine lens cDNA library. A 1.5 kb partial cDNA clone (pKEMC15) which encodes 471 amino acid residues of the bovine α3(IV) chain was obtained.

Comparative sequence analyses—Analysis of the pKEMC15 sequence reveals features common to all type (IV) collagen chains characterized to date. Within the 238 residues of the triple helical region encoded by pKEMC15 there are 3 imperfections in the regular Gly-Xaa-Yaa repeat sequence which coincide with interruptions in the corresponding regions of the α1(IV) and α2(IV) chains. In the 233 residues of the NC1 domain there are 12 conserved cysteine residues in identical positions to those in the other type (IV) collagens. There are several extended regions of sequence identity to these other chains and 71%, 61% and 70% overall homology with the human α1(IV), α2(IV) and α5(IV) chains. Therefore the results herein which provide the complete sequence of M2* and much of the collagenous domain of its parent molecule, support its previous designation as a type (IV) collagen.

Butkowski et al, (1990), *J. Lab. Clin. Med*, 115, 365-373, have recently sequenced a portion of the human M28+++ peptide which was obtained from collagenase digestion of human GBM. Of the 13 residues characterized by amino acid analysis, 12 are identical to the equivalent portion of the bovine sequence obtained from pKEMC15. Furthermore, the amino acid composition of the bovine α3(IV) NC1 domain predicted from the nucleotide sequence is very similar to that obtained from previous peptide sequencing of the human M28+++ fragment. This thus adds further evidence for the equivalence of the bovine M2* and human M28+++ fragments.

References

1. Timpl, R., Wiedemann, H., Van Delden, V., Furthmayr, H., and Kuhn, K. (1981) *Eur. J. Biochem.* 120, 203-211
2. Martin, G. R., Timpl, R., and Kuhn, K. (1988) *Adv. Protein Chem.* 39, 1-50
3. Timpl, R., (1989) *Eur. J. Biochem.* 180, 487-502
4. Hostikka, S. L., and Tryggvason, K. (1988) *J. Biol. Chem.* 263, 19488-19493
5. Soininen, R., Haka-Risku, T., Prockop, D. J., and Tryggvason, K. (1987) *FEBS Lett.* 225, 188-194
6. Muthukumaran, G., Blumberg, B., and Kurkinen, M. (1989) *J. Biol. Chem.* 264, 6310-6317
7. Saus, J., Quinones, S., Mackrell, A., Blumberg, B., Muthukumaran, G., Pihlajaniemi, T., and Kurkiven, M. (1989) *J. Biol. Chem.* 264, 6318-6324
8. Blumberg, B., MacKrell, A. J., and Fessler, J. H. (1988) *J. Biol. Chem.* 263, 18328-18337
9. Butkowski, R. J., Wieslander, J., Wisdom, B. J., Barr, J. F., Noelkan, M. E., and Hudson, B. G. (1985) *J. Biol. Chem.* 260, 3739-3747
10. Wieslander, J., Langeveld, J., Butkowski, R., Jodlowski, M., Noelken, M., and Hudson, B. G. (1985) *J. Biol. Chem*, 260, 8564-8570
11. Butkowski, R., Langeveld, J. P. M., Wieslander, J., Hamilton, J., and Hudson, B. G. (1987) *J. Bid. Chem.* 262, 7874-7877
12. Butkowski, R., Shen, G-Q., Wieslander, J., Michael, A. F., and Fish, A. J. (1980) *J. Lab. Clin. Med.* 115, 365-373
13. Saus, J., Wieslander, J., Langeveld, J. P. M., Quinones, S., and Hudson, B. G. (1988) *J. Biol. Chem.* 263, 13374-13380
14. Hudson, B. G., Wieslander, J., Wisdon, B. J. Jr., and Noelken, M. G. (1989) *Lab. Invest.* 61, 256-269
15. Kleppel, M. M., Michael, A. F. and Fish, A. J. (1986) *J. Biol. Chem.* 261, 16547-16552
16. Jeraj, K., Kim, Y., Vernier, R. L., Fish, A. J., and Michael, A. F. (1983) *Am. J. Kidney Dis.* II, 626-629
17. Kashtan, C., Fish, A. J., Kleppel, M., Yoshioka, K., and Michael, A. F. (1986) *J. Clin. Invest.* 78, 1035-1044
18. Kleppel, M. M., Kashtan, C. E., Butkowski, R. J., Fish, A. J., and Michael, A. F. (1987) *J. Clin. Invest.* 80, 263-266

19. Jenis, E. H., Valeski, J. E., Calcagno, P. L. (1981) *Clin. Nephrol.* 15, 111–114
20. Olson, D. L., Anand, S. K., Landing, B. H., Heuser, E., Grushkin, C. M., and Lieberman, E. (1980) *J. Pediatr.* 96, 697–699
21. Savage, C. O. S., Pusey, C. D., Kershaw, M. J., Cashman, S. J., Harrison, P., Hartley, B., Turner, D. R., Cameron, J. S., Evans, D. J., and Lockwood, C. M. (1986) *Kidney Int.* 30, 107–112
22. Hostikka, S. L., Eddy, R. L., Byers, M. G., Hoyhtya, M., Shows, T. B., and Tryggvason, K., (1990) *Proc. Natl. Acad. Sci. U.S.A.* 87, 1606–1610
23. Myers, J. C., Jones, T. A., Pohjolainen, E. R., Kadri, A. S., Goddard, A. D., Sheer, D., Solomon, E., and Pihlajaniemi, T. (1990) *Am. J. Hum. Genet.* 46, 1024–1033
24. Atkin, C. L., Hasstedt, S., Menlove, L., Cannon, L., Kirschner, N., Schwartz, C., Nguyenk, K. and Skolnick, M. (1988) *Am. J. Hum. Genet.* 42, 249–255
25. Brunner, H., Schroder, C., Van Bennekom, C., Lambermon, E., Tuerlings, J., Menzel, D., Olning, H., Monnens, L., Wieringa, B. and Ropers, H. H. (1988) *Kidney Int.* 34, 507–510
26. Szpiro-Tapia, S., Bobrie, G., Guilloud-Bataille, M., Heuertz, S., Julier, C., Frezal, J., Grunfeld, J. P. and Hors-Cayla, M. C. (1988) *Hum. Genet.* 81, 85–87
27. Flinter, F. A., Abbs, S., and Bobrow, M. (1988) *Genomics* 4, 335–388
28. Barker, D. F., Hostikka, S. L., Zhou, J., Chow, L. T., Oliphant, A. R., Gerken, S. C., Gregory, M. C., Skolnick, M. H., Atkin, C. L., and Tryggvason, K. (1990) *Science* 248, 1224–1227
29. Pihlajaniemi, T., Tryggvason, K., Myers, J. C., Kurkinen, M., Lebo, R., Cheung, M. C., Prockop, D. J., and Boyd, C. D. (1985) *J. Biol. Chem.* 260, 7681–7687
30. Gunwar, S., Saus, J., Noelken, M. E., and Hudson, B. G. (1990) *J. Biol. Chem.* 265, 5466–5469
31. Grunfeld, J. P. (1985) *Kidney Int.* 27, 83–92
32. Hinglais, N., Grunfeld, J. P., Bois, E. (1972) *Lab. Invest.* 27, 473–487
33. Yoshikawa, N., Cameron, A. H., White, R. H. R. (1981) *J. Pathol.* 135, 199–209

EXPRESSION

The general nature of vectors for use in accordance with the present invention is not crucial to the invention. In general, suitable vectors and expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Again, control sequences, such as recognition, promoter, operator, inducer, terminator and other sequences essential and/or useful in the regulation of expression, will be readily apparent to those skilled in the art. The vectors may be modified or engineered in any suitable manner.

In general, there are a number of methods which can be used to produce the peptide and nucleotide sequences of the invention. One straightforward method is simply to synthesize the appropriate nucleotide sequence, insert it into a suitable expression plasmid, transform a suitable host, culture the host, and obtain the peptide of the invention by any suitable means, such as sonication and centrifugation.

Alternatively, fragments can be obtained by digestion with the relevant restriction enzymes, and a suitable oligonucleotide ligated to the 5'-end coding for the missing amino acids. The resulting cDNA can then be used as above.

Other suitable methods will be apparent to those skilled in the art.

Ideally, the receiving vector has a ClaI site and a SalI site for each of insertion, but blunt-end ligation, for example, may also be used, although this may lead to uncertainty over reading frame and direction of insertion. In such an instance, it is a matter of course to test transformants for expression, 1 in 6 of which should be useable. Suitable vectors may be selected as a matter of course by those skilled in the art according t the expression system desired.

By transforming *E. coli* with the plasmid obtained, selecting the transformant with ampicillin or by other suitable means, and adding tryptophan or other suitable promoter inducer such as indoleacrylic acid, the desired protein may be expressed. The extent of expression may be analyzed by SDS polyacrylamide gel electrophoresis—SDS-PAGE (Nature, (1970), 227, pp.680–685).

It will also be appreciated that, where another vector is used, for example, it will be equally acceptable to employ a different selection marker or markers, or an alternative method of selection, and/or to use any suitable promoter as required or convenient.

After cultivation, the transformant cells are suitably collected, disrupted, for example, sonicated, and spun-down. Disruption may also be by such techniques as enzymic digestion, using, for example, cellulase, or by shaking with an agent such as glass beads, but methods such as sonication are generally preferred, as no additions are necessary.

Conventional protein purification is suitable to obtain the expression product.

Where not specifically described herein, methods for growing and transforming cultures etc. are usefully illustrated in, for example, Maniatis (Molecular Cloning, A Laboratory Notebook, Maniatis et al. [Ed's], Cold Spring Harbor Labs, New York).

Cultures useful for the invention may suitably be cultures of any living cells, and may vary from prokaryotic expression systems up to eukaryotic expression systems. One preferred prokaryotic system is that of *E. coli*, owing to its ease of manipulation. However, in general terms, it is preferable to express proteins intended for use in the human body in higher systems, especially mammalian cell lines. A currently preferred such system is the Chinese Hamster Ovary (CHO) cell line. Although this system tends not to be as easy to use as the *E. coli* system, its advantage lies in the processing of the protein after primary synthesis. *E. coli*, for example, does not have the equipment to glycosylate mammalian proteins, and it is preferred to glycosylate such proteins where possible, if for no other reason than that the natural proteins are glycosylated. In certain cases, glycosylation may be of no assistance whatever, and may even hinder the protein.

Other expression systems which may be employed include streptomycetes, for example, and yeasts, such as Saccharomyces spp., especially *S. cerevisiae*. With current progress in research, other systems are becoming available and there is no effective limit on which system is used, provided that it is suitable. The same systems may also be used to amplify the genetic material, but it is generally convenient or use *E. coli* for this purpose where only proliferation of the DNA is required.

DIAGNOSTICS

Labels for use in the present invention include, substances which have a detectable physical, chemical, or electrical property. When a detectable labeling substance is introduced, it can be linked directly such as by covalent bonds or can be linked indirectly such as by incorporation of the ultimately detectable substance in a microcapsule or liposome.

Labeling materials have been well-developed in the field of immunoassays and in general almost any label useful in such methods can be applied to the present invention. Particularly useful are enzymatically active groups, such as enzymes (see *Clin. Chem.*, (1976) 22:1232, U.S. Pat. Re. No. 31,006, and UK Pat. 2,019,408), enzyme substrates (see U.S. Pat. No. 4,492,751), coenzymes (see U.S. Pat. Nos. 4,230,797 and 4,238,565), and enzyme inhibitors (see U.S. Pat. No. 4,134,792); fluorescers (see *Clin. Chem.*, (1979) 25:353); chromophores; luminescers such as chemiluminescers and bioluminescers (see U.S. Pat. No. 4,380,580); specifically bindable ligands such as biotin (see European Pat. Spec. 63,879) or a hapten (see PCT Publ. 83-2286); and radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., ligands, enzymes, substrates, coenzymes and inhibitors). Far example, a cofactor-labeled species can be detected by adding the enzyme (or enzyme where a cycling system is used) for which the label is a cofactor and a substrate or substrates for the enzyme. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, beta-galactosidase, alkaline phosphatase and peroxidase.

EXAMPLE 1

Collagen α3(IV) hybridization probe

A PCR-based strategy was used to generate a bovine α3(IV) hybridization probe (Morrison et al. 1991). Degenerate sense and antisense primers were designed complementary to each end of the known 27 residue amine acid sequence of the bovine α3(IV) peptide chain. These were then used in a PCR reaction to amplify a 68 bp bovine genomic fragment (KEM68), KEM68 was then used to screen a λgt11 bovine lens cDNA library (Clontech) and a 1.5 kb partial cDNA clone obtained, encoding 238 residues of the triple helical domain and all 233 residues of the NC1 domain.

EXAMPLE 2

Screening of cDNA library

The 1.5 kb bovine cDNA clone was then used to screen an oligo-dT primed λgt10 human kidney cDNA library (Clontech), an oligo-dT primed λgt11 human kidney cDNA library and a random primed human kidney cDNA library. Of $3 \times 10^5$ clones screened in each library, only one positive clone was obtained, from the human kidney cDNA library (Clontech). The secondary from this positive was eluted into 500 μl of buffer (100 mM NaCl, 8 mM $MgSO_4 7H_2O$, 50 mM TrisCl, pH7.5 and 0.01% gelatin). 2 μl of this was used as a template for PCR with primers complementary to the β-galctosidase portion ot the λgt10 template. The amplified product, KMC27 was digested with EcoR1 and cloned into the EcoR1 site of pBluescript (Stratagone). The sequence was obtained using T7 polymerase (Sequenase) with T7 and T3 sequencing primers and 17-residue oligonucteotide primers designed from known sequences of the inserts, according to standard protocols.

EXAMPLE 3

Chromosomal assignment
Southern blot hybridization of α3(IV) probe to rodent x human hybrids.

Chromosomal assignment of the human α3(IV) gene was performed using a panel of 11 human-Chinese hamster hybrids. DNA from human and Chinese hamstar parental cell lines and human x rodent hybrids was digested to completion with Pst1. The DNA was fractionated by electrophoresis on a 0.9% agarose gel and blotted onto Hybond N+ (Amersham International). A 1.7 kb 5' portion of the cDNA KMC27 was labelled with [α-$^{32}$P]dCTP by random primer labelling (Feinberg and Vogelstein, 1983) and hybridized to the filter bound DNAs in Church and Gilbert buffer (0.5M $Na_2HPO_4$, 7% SDS, 1% BSA, 1 mM EDTA) at 65° C. The filters were then washed in 0.1% SDS and 1×SSC (0.5M NaCl, 0.015M Na Citrate, pH7.0) and exposed to film for 3 days.

Northern Analysis

Total RNA was isolated from snap-frozen bovine 60 day old calf tissues using an acid guanidinium thiocyanate/phenol/chloroform extraction procedure (Chomczynski and Sacchi, 1987). 5–10 μg was electrophoresed on a 1.2% agarose gel containing formaldehyde, blotted to nitrocellulose and hybridized with KEMC15, the bovine COL4A3 probe. Washing was in 0.1% SDS, 0.5×SCC at 65° C. and the filter exposed to film for 2 days. pA+ RNA was isolated from total RNA using an oligo dT column (Collaborative Research Inc, Waltham, Mass.).

EXAMPLE 4

Isolation of cDNA clones

To generate an α3(IV) hybridization probe, use was made of the 27 residue amino acid sequence of the bovine α3(IV) chain, as no human α3(IV) amino acid sequence was currently available (Saus et al. 1988). The polymerase chain reaction was used to amplify a 68 bp segment corresponding to the bovine sequence. A longer bovine cDNA clone (KEMC15) was then obtained from a bovine line library. KEMC15 encodes 238 residues of the triple helical region and the complete 233 residues of the NC1 domain. Applicants anticipated that the bovine and human α3(IV) amino-acid sequences would be highly conserved in this region (Butkowski et al. (1990) have subsequently shown conservation of eleven residues in a twelve residue stretch). Therefore applicants used the bovine clone to screen for human homologs. On screening $3 \times 10^5$ clones of each of 3 human kidney cDNA libraries with KEMC15, only 1 positive clone, KMC27, was obtained.

EXAMPLE 5

Nucleotide sequence of α3(IV) cDNA

Sequence analysis of the cDNA clone KMC27 reveals an open-reading frame which, on translation, encodes 220 carboxy terminal residues of the NC1 domain of α3(IV) and ~2000 bp of the 3' untranslated region. As anticipated, within the coding region, the bovine and human sequences are very similar, with 90.5% homology at the nucleotide level and 93% homology at the amino acid level. Only 2 of the 15 non-identical amino acid residues are non-conservative substitutions. The homology of the sequence encoded by KMC27 with the bovine COL4A3 sequence, confirms its identity as a portion of the human COL4A3 gene. The amino acid composition of the NC1 domain of α3(IV) derived from the sequence of KMC27 is similar to that obtained from amino acid composition analysis of the human M28+++ fragment (Butkowski et al. 1990).

EXAMPLE 6

Comparative sequence analysis

Analysis of pKMC27 reveals features common to all type IV collagens characterized to date. In the 220 residues of the NC1 domain there are 12 conserved cysteine residues in identical positions to those in the other type IV collagens. Overall the sequence shows 71%, 60% and 70% amino acid identity with the NC1 domains of the human α1(IV), α2(IV) and α5(IV) chains respectively.

It has been suggested that the NC1 domains of α1(IV) and α2(IV) are the result of an intragenic duplication, as each consists of two equal-sized internal repeats, each containing 6 cysteine residues in invariant positions (Brinker et al. 1985; Pihlajaniemi et al. 1985; Myers et al. 1987). In the α1(IV) NC1 there are 45 (out of 229) positions in which the amino acid is identical between the two halves (Brinker et al. 1985; Pihlajaniemi et al. 1985) compared with 50 positions in the α2(IV) NC1 (out of 230) and 43 in the α5(IV) NC1 (Pihlajaniemi et al. 1990). Alignment of the corresponding internal repeats in the =3(IV) chain shows that 45 amino acids are conserved between the putative duplicated halves of the NC1 domain, including all twelve cysteine residues. Of the 116 amino acid residues conserved between all 4 chains, 62 are also conserved between the 'duplicated halves' of the NC1 domain in duplications.

As Dion and Myers (1985) have speculated, the conserved elements may play a role in the assembly of triple helical molecules, while the variable regions may be operative in discriminant chain selection. This may aid in the search for that portion of the α3(IV)NC1 responsible for the Goodpasture epitope. Comparing the last 219 residues of the NC1 domains of α1 (IV), α2(IV), α3(IV) and α5(IV), there are 46 positions in which the sequence of only one chain differs from the other 3; of these 46, 3 are a divergence of the α1 chain, 26 are a divergence of the α2 chain, 16 are a divergence of the α3 chain and one a divergence of the α5 chain alone. None of these divergences is duplicated, suggesting that intragenic gene duplication to form a complete NC1 domain preceded the evolution of the different type IV collagen chains.

EXAMPLE 7

Chromosomal Localization
Human x Rodent Somatic Cell Hybrids

To localize COL4A3, a panel of Chinese hamster x human somatic cell hybrids was analysed by Southern blot hybridization with a portion, KMC17, of the human KMC27 cDNA, as a probe. KMC17 detects a band of 11 kb in the Chinese hamster DNA and a band of 9 kb in the human DNA. The panel shown maps KMC17 to chromosome 2.

In Situ Hybridization

The α3(IV) gene was independantly mapped by in situ hybridization of the KMC17 cDNA clone to human metaphase chromosomes.

Northern Analysis

The bovine cDNA clone KMC15 which encodes 471 residues of the bovine α3(IV) chain, was used to probe a Northern blot of total RNA from bovine lung, liver and kidney. The gene codes for a single transcript of approximately 8.1 kb, the signal being equally intense in total RNA from lung and kidney, but absent in liver. Using 10 μg of polyA+ selected RNA a similar result was obtained, with similar intensity of hybridization in lung and kidney and a very faint signal obtained from liver RNA (data not shown). This is compatible with the observation that patients with Goodpasture syndrome show pathology in the lung and kidney, but no discernible liver abnormality.

EXAMPLE 8

DETERMINATION OF THE MOLECULAR STRUCTURE OF THE GP-AUTOANTIBODY COMBINING SITE (EPITOPE).

The epitope which reacts with GP-antibodies resides on monomeric and dimeric forms of the NC1 domain of the α3 chain of type IV collagen. The epitope contains a critical disulfide bond that is required for binding of GP antibodies. Knowledge of the epitope structure will yield information required for the development of diagnostic procedures for the detection of GP antibodies and development of therapeutic procedures for the removal of the toxic GP antibodies from blood plasma.

In applicants' search for the molecular identity of the GP epitope, applicants have employed mild chemical modification with a biotinylating reagent (sulfosuccinimidyl 6-biotinamido hexamoate [NHS-LC-Biotin]) which is highly specific for lysine and N-terminal amino acid residues. Lysine was selected because of the important role played by reactive amino groups in protein structure that ultimately dictates immunogenicity. The D2 fraction of NC1 hexamer, comprised of dimeric subunits reacting with GP-antibodies were biotinylated with the reagent and the products were analyzed by Western blotting with GP-sera (FIG. 1). Biotinylation abolished the reactivity of the dimeric subunits with GP sofa. These results indicate that lysine is a critical residue of the epitope structure.

Figure 2:
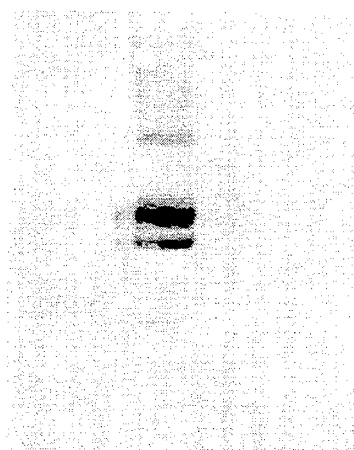
FIG. 2 is a Western Blot of the Control D1 (lane 1) and Carboxypeptidase Y treated D2 (lane 2), using GP sera.

Applicants also investigated the influence of carboxypeptidase treatment on the reactivity of the dimer subunits with GP sera. As shown in FIG. 2, this treatment also abolished reactivity with GP sera. These results suggest that the carboxy terminus is an important element of the epitope structure.

In addition to these structural features (disulfide bond, lysine, and carboxy terminus), the epitope is expected to be distinct in amino acid sequence from an analogous region of the other known chains (α1, α2, & α5) of type IV collagen and to likely have a hydrophilic character. Based on molecular cloning studies, a region at the carboxy terminus of the NC1 domain of the α3 chain was identified that fits these five criteria. Its structure for human α3 is:

ISRCQVCMKKRH (SEQ ID NO:3)

This 12 Mer peptide was chemically synthesized with the two cysteine residues blocked. The peptide was tested with ELISA measurements, as shown below, and found to be reactive with GP antibodies.

EXAMPLE 9

REACTIVITY OF α3 SYNTHETIC PEPTIDE WITH GP ANTIBODIES.

Figure 3:
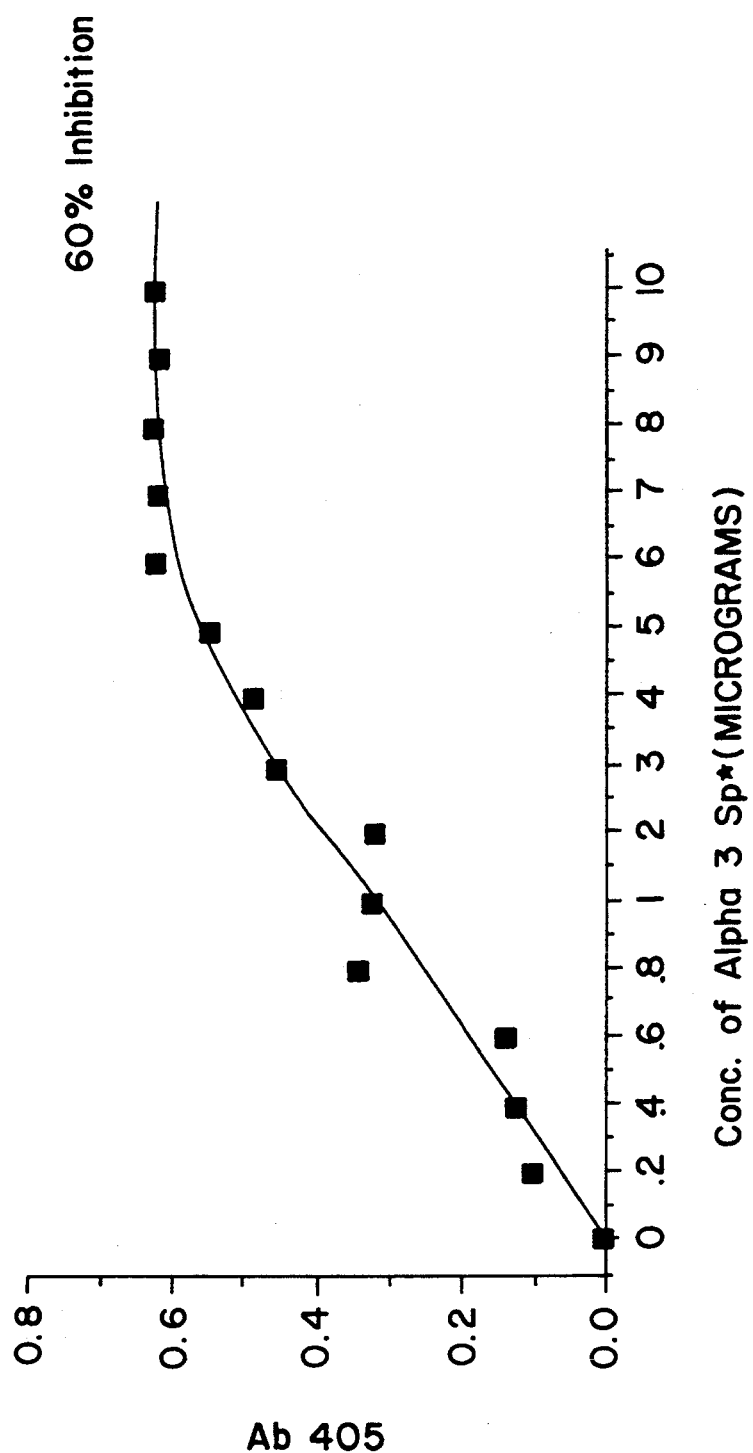
FIG. 3 is a graph depicting the results of an inhibition Elisa. The plates were coated with 400ngs of α3NC1 monomer (Goodpasture antigen) and subsequently blocked with 1% BSA. The primary antibody was preincubated with peptide for 12 hours and then the reaction mixture was treated with the Goodpasture antigen. Secondary antibodies were against human IgG and HRP conjugated. The assay was measured at Ab 405.

The reactivity was tested with anti sera from two GP patients using two different inhibition ELISA procedures. In FIG. 3, the peptide was preincubated with GP antibodies for 12 hours and the mixture then reacted with authentic GP antigen (α3 NC1 bovine monomer). The results show 60% inhibition at saturation (peptide concentration=5.4 $10^{-6}$ molar). This information suggests that the peptide binds the GP antibody and thus represents a portion of the native epitope.

The reactivity of the peptide was also tested by another procedure where the peptide was allowed to compete with the GP antigen for binding with GP antibodies for 12 hours. The results show 42% inhibition. As control, N-terminal peptides (10 Mer) from α1, α2, α3, & α4 NC1 domains were tested for reactivitity, and the results showed no inhibition. These results further indicated that the α3 carboxy terminal peptide uniquely binds the GP antibody.

Figure 4:
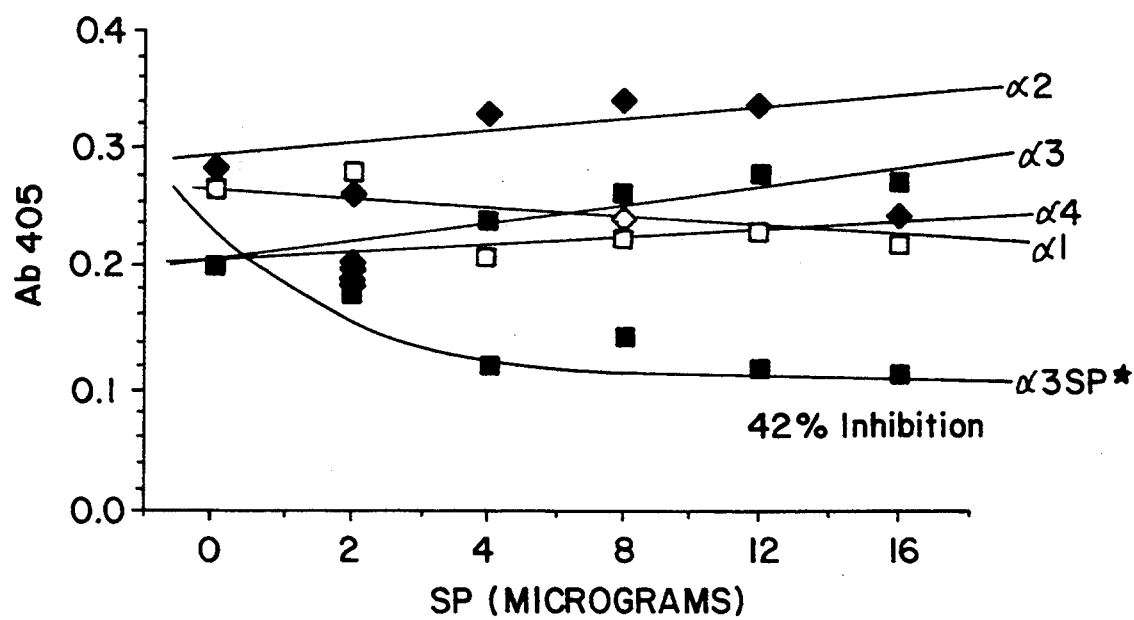
FIG. 4 is a graph depicting the results of an inhibition ELISA. The same conditions as in FIG. 3 were used, except in this case the peptide was allowed to compete with the Goodpasture (GP) antigen for GP antibodies for 12 hours.

Overall, these ELISA results indicate that the α3 carboxy terminal peptide represents a portion of the native epitope (see FIG. 4).

EXAMPLE 10

DEVELOPMENT OF DIAGNOSTIC PROCEDURE FOR THE DETECTION OF GP ANTIBODIES IN HUMAN SERA.

Figure 5:
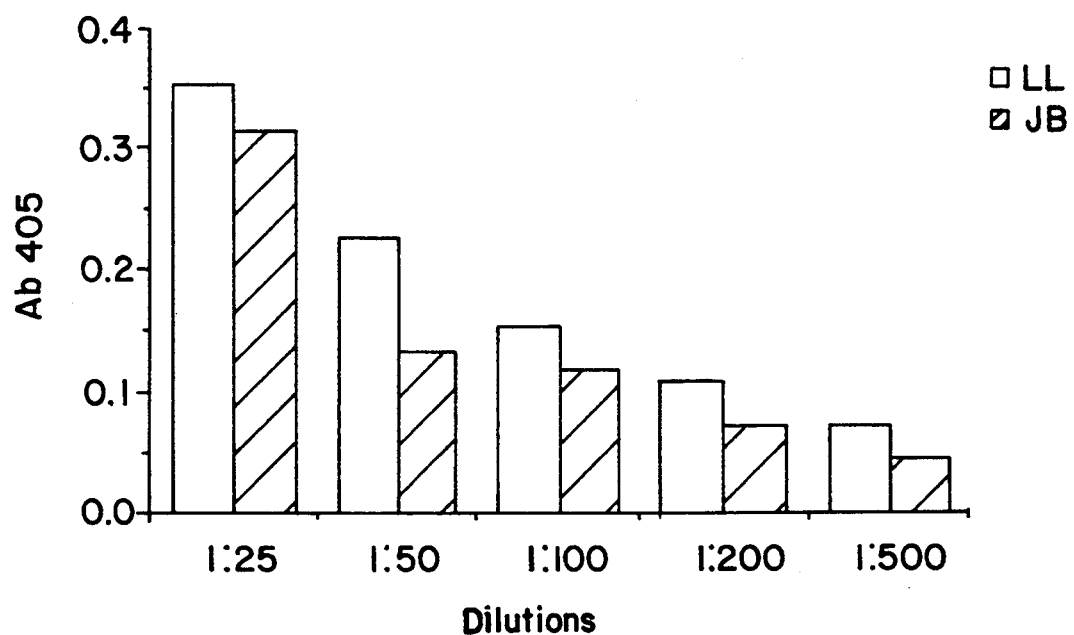
FIG. 5 is a graph which depicts the results of a direct ELISA to test the binding of Sp* to GP antibodies. The plates were coated with 20 micrograms of peptide and analyzed for its reactivity with the GP antibodies. The other conditions are same as FIG. 3.

The α3 carboxy terminal peptide was allowed to bind to ELISA plates and tested for reactivity with GP antibodies using a direct ELISA procedure. Using two GP seras, as shown in FIG. 5, the peptide bound antibody in a dose dependent manner. This indicates that the peptide can be used as a diagnostic tool for the detection of GP antibodies in blood plasma.

EXAMPLE 11

DEVELOPMENT OF A THERAPEUTIC PROCEDURE FOR THE REMOVAL OF GP ANTIBODIES FROM BLOOD PLASMA.

Figure 6:
FIG. 6 is a Western blot analysis of the reactivity of Goodpasture antigen (α3NC1 Monomer) with the peptide bound GP antibodies from a cynogen bromide activated Sepharose 4B column. 1 mg of α3 peptide was coupled to the matrix for 12 hours upon packing it on a column, GP sera (1:10 dilution) was repeatedly passed through the column for 5 times and the non-specifically bound antibodies removed, upon which the bound antibodies were eluted at low pH and immediately neutralized and dialysed against 1X PRS pH 7.4. This sample was then used for a Western blot analysis.

The α3 carboxy terminal peptide was bound to cyanogen bromide activated Sepharose 4B column. The column was then tested for specific binding of GP antibodies from sera. The bound antibodies were eluted and tested for reactivity with GP antigen by Western blotting (FIG. 6). The results show distinct reactivity with the GP antigen. This indicates that the peptide can be used to prepare a immunoabsorbent column to selectively remove toxic antibodies from blood plasma of patients with GP snydrome.

EXAMPLE 12

Primer design for the generation of collagen α3(IV) hybridization probes—Two PCR based strategies were used to generate hybridization probes. Both made use of the known 27 residue amino acid sequence of the bovine α3(IV) chain. Firstly, four degenerate sense primers (17-22mers) were designed corresponding to regions of the known bovine α3(IV) sequence that were most distinct from the corresponding α1(IV) and α2(IV) sequences (FA,FB,FC,FD). Antisense primers were then designed to be complementary to regions of the NC1 that are highly conserved between the human and mouse α1 (IV) and α2(IV) chains, in anticipation that such homology would extend to the α3(IV) chain (RA,RB,RC,RD). The second strategy involved using degenerate (32-fold) sense primers (17mers), corresponding to the amino acids near the amino terminal end of the known 27 residue sequence of bovine α3(IV) (F1,F2,F3,F4). Similarly degenerate oligonucleotide antisense primers were also designed, corresponding to the amino acids at the carboxyl end of the known sequence (R1,R2,R3,R4) (FIG. 7).

EXAMPLE 13

PCR protocols—Standard PCR reactions were performed in a 50 μl volume containing 10–20 ng of either bovine genomic, human genomic or human cDNA template, 25 pmols of each oligonucleotide primer, 200 μM of each dNTP, 50 mM KCl, 10 mM Tris (pH 8.3), 1.5 mM $MgCl_2$, 0.01% gelatin and 1.25 units of Tag polymerase (Perkin Elmer Cetus). Samples were overlaid with 50 μl mineral oil. Routinely, 35 cycles of PCR were performed. With primers FA–FD and RA–RD, annealing was performed at 60° C. for 1 minute, extension at 72° C. for 2 minutes and denaturation at 94° C. for 1 minute, with a final extension time of 10 minutes. With primers F1–F4 and R1–R4, annealing was for 30 seconds at 68° C. for the first cycle, at 66° C. for 30 seconds second, at 64° C. for 30 seconds for the third and at 58° C. for the fourth and subsequent cycles. No extension step was performed as the predicted product was only 68 base pairs. Denaturation was carried out at 94° C. for 1 minute.

EXAMPLE 14

Subcloning and sequencing. The 68 bp product obtained using primers F4 and R3 and bovine genomic template (KEM68) was cloned into the EcoRV site of the phagemid pBluescript II (Stratagene). The double-stranded plasmid, pKEM68, was sequenced using T7 polymerase (Sequenase) with T7 and T3 sequencing primers according to standard protocols.

EXAMPLE 15

Screening of cDNA library—KEM68 was labelled by PCR. A 50 μl reaction was performed containing 5 pmoles of primers F3 and R4, 50pg of pKEM68, 10 μM dATP, dGTP, dTTP and 9.4 μM dCTP. 10 μl of [α-$^{32}$P]dCTP (3000 Ci/mmol) was added to give a final concentration of 0.6 μM. Standard buffer and 1 unit of Tag polymerase were used and 30 cycles of amplification performed. The reaction product was passed through a G25 column to remove most of the unincorporated primers. The labelled product was used to screen a λgt11 bovine lens cDNA library (Clontech). A total of 3×10⁵ clones were screened and 16 positives obtained. Secondaries from these positives were eluted into 500 μl of buffer (100 mM NaCl, 8 mM $MgSO_4$·$7H_2O$, 50 mM TrisCl,pH7.5 and 0.01% gelatin). 2 μl of eluant was used as a template for PCR with primers complementary to the β-galactosidase portion of the λgt11 template. The largest of the 16 amplified products, KEMC15, was sequenced directly using the same λgt11 primers as in its initial amplification. KEMC15 was subsequently cloned into the EcoRV site of pBluescript II (Stratagene). The complete sequence was obtained using 17-residue oligonucleotide primers designed from known sequences of the insert (FIG. 9).

EXAMPLE 16

Collagen α3(IV) hybridization probe—The known 27 residue amino acid sequence of the junction between the collagenous and NC1 domains of bovine α3(IV) was used to generate an α3(IV) hybridization probe (Saus at al, (1988) *J. Biol. Chem.*, 263, 3374–13380). As the number of nucleotide sequences that may encode this peptide segment is very large, highly degenerate oligonucleotide probes would be required to include all coding possibilities. Consequently, two PCR based strategies were adopted.

In the first approach, primers were designed to correspond to regions of the known 27 amino acid sequence of bovine α3(IV) that is most distinct from the corresponding portion of α1(IV) and α2(IV) (FA-FD). On this basis, the most suitable sense primers corresponded to the carboxy terminal region of the known sequence, allowing no room for an antisense primer to be designed complementary to the known residues. Therefore, use was made of the number of highly conserved stretches of 6–7 amino acids in the NC1 domain of α1(IV) and α2(IV), which are also conserved between species. If such sequences represent essential structural elements of type (IV) collagen, it might be assumed that such homology would extend to α3(IV). 17–20mers (RA-RD) complementary to portions of these conserved regions were therefore designed. Where α1(IV) and α2(IV) differed in these regions, a degenerate oligonucleotide was synthesized. By intention, the maximum degeneracy of these antisense primers was only 4-fold. Using various combinations of primers FA-FD and RA-RD and standard PCR protocols, products of the "correct" size were obtained using a human cDNA template, and discrete products of various sizes obtained using either human or bovine genomic templates. However, sequence analysis of these products revealed them to be portions of genes encoding α1(IV), or α2(IV).

A second strategy was therefore adopted which did not rely on the assumed homology of regions of the NC1 domain of α3(IV) with α1(IV) and α2(IV). In this approach, sense and antisense primers were designed complementary to each end of the known 27 amino acid protein sequence. As the peptide sequence is so short, there was little latitude in the design of these primers. The 3'ends of the primers had to be as distinct as possible from the corresponding regions of α1(IV) and α2-(IV), to avoid amplification of these known collagen genes. Four sense primers, F1–F4, were synthesized according to the amino acid sequence lys-pro-gly-asp-thr-gly (SEQ ID NO: 22), near the amino terminal end of the known sequence. AAG was used for lysine, based on codon usage frequencies in collagens. All codons for proline, glycine and asparagine were included. Four separate sense primers were synthesized, each using a different nucleotide as the wobble base of threonine, to eliminate degeneracy from the five nucleotides at the 3' end of the primers. Antisense primers were synthesized complementary to the amino-acid sequence tyr-his-arg-phe-ala-val-phe (SEQ ID NO: 23), near the carboxy terminus of the peptide sequence. Again, four primers were made to eliminate degeneracy from the five 3'most nucleotides. Two of the primers (R1 and R2) incorporated the complement of the codons CG(A/C/G/T) for arginine, and two (R3 and R4), the complement of AG-(A/G) for arginine (FIG. 7).

Standard 3-step PCR protocols (denature, anneal, extend) and combinations of the degenerate primers F1–F4 and R1–R4 did not yield an amplification product of the correct (predicted) size from a bovine or human genomic template or human cDNA template. The use of degenerate primers precludes the calculation of a specific predicted annealing temperature and therefore, experiments were performed with a range of annealing temperatures. Despite the use of stringent annealing temperatures and short (15 sec) annealing times, in practice many products of up to 2000 base pairs in size were generated. In an attempt to reduce the complexity of the PCR products, a PCR cycling profile with stepwise reductions in annealing temperature was adopted. The goal of the stepwise protocol is to reduce spurious amplification products during early cycles. Once a double-stranded product has been formed by PCR, regardless of the match between primer and template, that product is a perfect template for primer annealing in subsequent cycles. The use of high initial annealing temperatures reduces spurious binding of primer and increases the proportion of correct annealing, but does so at the expense of the efficiency of generation of 'correct' product. After early cycles of stringent amplification have increased the proportion of desired product in the mix, subsequent reduction of the annealing temperature allows a more efficient amplification to occur.

FIG. 8a shows an example of the PCR products obtained using combinations of the primers F1–F4 and R3, using a standard PCR cycling profile. No product of 68 base pairs is evident in any of the reactions using the degenerate primers. As FIG. 8b shows, by reducing the annealing temperature in a stepwise fashion, a 68 base pair product is clearly obtained when primers F2 and R3 or F4 and R3 are used. For non-degenerate primers, such as F9* and R9*, which are exactly complementary to portions of α1(IV), the "correct" product is obtained using both cycling profiles.

EXAMPLE 17

Nucleotide sequence of α3(IV) cDNA—The 68 base pair fragment obtained using primers F4 and R3 and bovine genomic template, KEM68, was then cloned. Sequence analysis of pKEM68 revealed an open reading frame which, on translation, codes for a peptide sequence identical to the known peptide sequence of α3(IV). A bovine lens cDNA library was then screened with KEM68 yielding 16 positive clones of 0.5–1.5 kb. A partial restriction map of the longest clone, pKEMC15, is shown in FIG. 9. DNA sequencing of pKEMC15 showed that the clone codes for the known α3(IV) amino acid sequence with the exception of a serine-for-tyrosine substitution at the 15th amino acid of the NC1 domain. Subsequently, Gunwar et al, (1990), *J. Biol. Chem*, 265, 5466–5469 have published a second partial amino acid sequence of α3(IV) in which a serine was also found at position 15. Furthermore, an additional four amino acids were obtained by Hudson et al and these were the same as the amino acids predicted from the nucleotide sequence of clone pKEMC15.

pKEMC15 encodes all of the NC1 domain as well as 238 amino terminal residues of the collagenous repeat sequence Gly-Xaa-Yaa and 8 base pairs of the 3' untranslated region. Table 1 shows the amino-acid composition of NC1 α3(IV) derived from the sequence of pKEMC15 compared to that obtained from amino acid analysis of bovine M2* and human M28+++.

TABLE 1

Comparison of amino acid compositions of collagenase-resistant fragments from basement membrane with the composition of the bovine α3(IV) NC1 domain predicted from nucleotide sequence.

| Amino acid | Number of residues | | |
|---|---|---|---|
| | α3(IV) | M2* | M28+++ |
| Alanine | 20 | 18.5 | 19.2 |
| Phenylalanine | 15 | 14.1 | 16.9 |
| Lysine | 5 | 4.7 | 6.2 |
| Proline | 20 | 21.7 | 17.7 |
| Threonine | 15 | 14.7 | 19.3 |
| Cysteine | 12 | NE | NE |
| Glycine | 19 | 24.9 | 22.5 |
| Leucine | 15 | 17.1 | 18.2 |
| Glutamine/Glutamic acid | 19 | 21.3 | 20.6 |
| Valine | 8 | 9.2 | 10.4 |
| Asparagine/Aspartic acid | 14 | 14.2 | 14.5 |
| Histidine | 4 | 5.2 | 6.6 |
| Methionine | 9 | 7.3 | 3.0 |
| Arginine | 12 | 12.1 | 14.1 |
| Tryptophan | 4 | NE | NE |
| Isoleucine | 14 | 10.7 | 11.1 |
| Serine | 23 | 21.4 | 18.5 |
| Tyrosine | 7 | 6.9 | 6.2 |

Composition of M2* is from Butkowksi et al, (1985), J. Biol. Chem., 260, 8564–8570.
Composition of M28+++ is from Butkowski et al (1980), J. Lab. Clin. Med. 115, 365–373.
NE: no amino acid determination made.

EXAMPLE 18

Comparative Sequence Analyses—The deduced amino acid sequence reveals several features typical of type IV collagens. The NC1 domain is similar in length to α1(IV), α2(IV) and α5(IV) and contains 12 cysteine residues in identical places. Regions that are highly conserved between α1(IV), α2(IV) and α5(IV) are also highly conserved in α3(IV). The three imperfections in the Gly-Xaa-Yaa repeat sequence found in the 238 residues of the triple helical region abutting the NC1 domain in α3(IV) occur at identical points of the collagenous domain in human α1(IV), α2(IV) and α5(IV). Overall the sequence shows 71%, 60% and 70% amino acid identity with the NC1 domains of the human α1-(IV), α2(IV) and α5(IV) chains.

It will be appreciated that the instant specification is set forth by way of illustration and not limitation, and that various modifications and changes may be made without departing from the spirit and scope of the present invention.

What is claimed:

1. An isolated and substantially pure polynucleotide encoding 238 amino acids of the carboxy terminal end of the triple helical domain and all 233 amino acids of the carboxy terminal noncollagenous domain of the bovine α3 chain of type IV collagen.

2. An isolated and substantially pure polynucleotide encoding 218 amino acids of the carboxy terminal noncollagenous domain of the human α3 chain of type IV collagen.

3. An isolated and substantially pure nucleotide having the following sequence SEQ. ID. No. 1 of nucleotides:

| 1 | ggc | ctc | cct | ggc | agg | aaa | ggg | cca | gtg | gga | gat | gct | ggg | cct | cca | ggc | 48 |
|---|---|---|---|---|---|---|---|---|---|---|---|---|---|---|---|---|---|
| | Gly | Leu | Pro | Gly | Arg 5 | Lys | Gly | Pro | Val | Gly 10 | Asp | Ala | Gly | Pro | Pro 15 | Gly | |
| 49 | cag | ctt | ggc | gtg | aca | gga | cct | caa | ggg | gca | cca | ggc | ttt | cct | ggt | gta | 96 |
| | Gln | Leu | Gly | Val 20 | Thr | Gly | Pro | Gln | Gly 25 | Ala | Pro | Gly | Phe | Pro 30 | Gly | Val | |
| 97 | acc | atc | cct | ggc | cag | aaa | gga | gat | cga | ggt | cca | cct | ggc | tcc | aga | gga | 144 |
| | Thr | Ile | Pro 35 | Gly | Gln | Lys | Gly | Asp 40 | Arg | Gly | Pro | Pro | Gly 45 | Ser | Arg | Gly | |
| 145 | aac | cca | ggc | atg | cct | ggt | cct | cct | gga | cct | cca | ggg | agt | cct | gta | gaa | 192 |
| | Asn | Pro 50 | Gly | Met | Pro | Gly | Pro 55 | Pro | Gly | Pro | Pro | Ggy 60 | Ser | Pro | Val | Glu | |
| 193 | ggc | ata | aaa | gga | gac | aag | ggg | ttg | atg | gga | gag | cct | ggc | caa | aga | ggt | 240 |
| | Gly 65 | Ile | Lys | Gly | Asp | Lys 70 | Gly | Leu | Met | Gly | Glu 75 | Pro | Gly | Gln | Arg | Gly 80 | |
| 241 | cca | cct | gga | gct | ata | gga | gac | atg | ggg | tca | cca | ggt | cat | ccg | gga | gca | 288 |
| | Pro | Pro | Gly | Ala | Ile 85 | Gly | Asp | Met | Gly | Ser 90 | Pro | Gly | His | Pro | Gly 95 | Ala | |
| 289 | cca | ggt | gtc | ccc | ggt | cag | cca | ggg | gcc | aga | ggt | gat | cct | gga | ttc | tat | 336 |
| | Pro | Gly | Val 100 | Pro | Gly | Gln | Pro | Gly 105 | Ala | Arg | Gly | Asp | Pro 110 | Gly | Phe | Tyr | |
| 337 | gga | ttt | cca | ggc | atg | aaa | ggg | aag | aag | ggt | aat | tca | gga | ttt | cca | gga | 384 |
| | Gly | Phe | Pro 115 | Gly | Met | Lys | Gly | Lys 120 | Lys | Gly | Asn | Ser | Gly 125 | Phe | Pro | Gly | |
| 385 | cca | cct | gga | cct | cca | ggg | caa | agt | gga | cca | aaa | gga | cca | cct | gga | gta | 432 |
| | Pro | Pro 130 | Gly | Pro | Pro | Ggy | Gln 135 | Ser | Gly | Pro | Lys | Gly 140 | Pro | Pro | Gly | Val | |
| 433 | cgt | gga | gag | cct | ggc | aca | gtg | aag | atc | atc | tcc | ctt | cca | gga | agc | cca | 480 |
| | Arg 145 | Gly | Glu | Pro | Gly | Thr 150 | Val | Lys | Ile | Ile | Ser 155 | Leu | Pro | Gly | Ser | Pro 160 | |
| 481 | ggc | cca | cct | ggt | tca | gct | gga | gaa | cca | ggg | atg | caa | gga | gaa | ccc | ggg | 528 |
| | Gly | Pro | Pro | Gly | Ser 165 | Ala | Gly | Glu | Pro | Gly 170 | Met | Gln | Gly | Glu | Pro 175 | Gly | |
| 529 | ccc | cca | gga | cca | cca | gga | gat | cca | gga | ccc | tgt | ggg | cca | aaa | ggt | aaa | 576 |

-continued

| | | | | | | | | | | | | | | | | |
|---|---|---|---|---|---|---|---|---|---|---|---|---|---|---|---|---|
| | Pro | Pro | Gly | Pro 180 | Pro | Gly | Asp | Pro | Gly 185 | Pro | Cys | Gly | Pro | Lys 190 | Gly | Lys |
| 577 | cca Pro | ggg Gly | gag Glu 195 | gat Asp | ggt Gly | cca Pro | cca Pro | gga Gly 200 | act Thr | cct Pro | gga Gly | cca Pro | act Thr 205 | gga Gly | gaa Glu | aaa Lys | 624 |
| 625 | ggc Gly | aac Asn 210 | aaa Lys | ggt Gly | tgt Cys | aaa Lys | gga Gly 215 | gag Glu | caa Gln | gga Gly | cca Pro | cat Pro 220 | gga Gly | tcc Ser | gat Asp | ggc Gly | 672 |
| 673 | atg Leu 225 | cca Pro | ggc Gly | ttg Leu | aag Lys | ggg Gly 230 | aaa Lys | cct Pro | gga Gly | gac Asp | act Thr 235 | gga Gly | cca Pro | cct Pro | gca Ala | gca Ala 240 | 720 |
| 721 | ggg Gly | gca Ala | gtg Val | atg Met | agg Arg 245 | ggc Gly | ttt Phe | gtc Val | ttt Phe | acc Thr 250 | cgg Arg | cac His | agc Ser | cag Gln | acc Thr 255 | aca Thr | 768 |
| 769 | gca Ala | att Ile | ccc Pro | tcc Ser 260 | tgt Cys | cca Pro | gaa Glu | ggg Gly | aca Thr 265 | gag Glu | ccg Pro | ctc Leu | tat Tyr | agt Ser 270 | ggg Gly | ttt Phe | 816 |
| 817 | tct Ser | ctt Leu | ctc Leu 275 | ttt Phe | gta Val | caa Gln | gga Gly | aat Asn 280 | gaa Glu | caa Gln | gcc Ala | cat His | gga Gly 285 | cag Gln | gac Asp | ctg Leu | 864 |
| 865 | gga Gly | aca Thr 290 | ctt Leu | ggc Gly | agc Ser | tgc Cys | ctg Leu 295 | cag Gln | cga Arg | ttt Phe | acc Thr | aca Thr 300 | atg Met | cca Pro | ttc Phe | tta Leu | 912 |
| 913 | ttc Phe 305 | tgc Cys | aat Asn | atc Ile | aac Asn | gat Asp 310 | gta Val | tgt Cys | aat Asn | ttt Phe | gca Ala 315 | tct Ser | cga Arg | aac Asn | gat Asp | tat Tyr 320 | 960 |
| 961 | tca Ser | tac Tyr | tgg Trp | ctg Leu | tca Ser 325 | aca Thr | cca Pro | gct Ala | atg Met | ata Ile 330 | cca Pro | atg Met | gac Asp | atg Met | gct Ala 335 | cca Pro | 100 |
| 1009 | att Ile | act Thr | ggc Gly | agg Arg 340 | gcc Ala | atg Leu | gag Glu | cct Pro | tat Tyr 345 | att Ile | agc Ser | aga Arg | tgt Cys | aca Thr 350 | gtc Val | tgt Cys | 105 |
| 1057 | gaa Glu | ggt Gly | cct Pro 355 | gca Ala | att Ile | gcc Ala | ata Ile | gct Ala 360 | gtt Val | cac His | agc Ser | caa Gln | acc Thr 365 | act Thr | gat Asp | atc Ile | 110 |
| 1105 | ccc Pro | ccc Pro 370 | tgt Cys | cct Pro | gct Ala | ggc Gly | tgg Trp 375 | att Ile | tct Ser | ctc Leu | tgg Trp | aaa Lys 380 | ggc Gly | ttt Phe | tct Ser | ttc Phe | 115 |
| 1153 | atc Ile 385 | atg Met | ttc Phe | aca Thr | agt Ser | gct Ala 390 | ggt Gly | tcg Ser | gag Glu | ggt Gly | gct Ala 395 | ggg Gly | caa Gln | gca Ala | ctc Leu | gca Ala 400 | 120 |
| 1201 | tcc Ser | ccc Pro | ggc Gly | tcc Ser | tgc Cys 405 | ctg Leu | gaa Glu | gaa Glu | ttc Phe | cga Arg 410 | gcc Ala | agt Ser | cca Pro | ttt Phe | ata Ile 415 | gaa Glu | 124 |
| 1249 | tgt Cys | cac His | gga Gly | aga Arg 420 | gga Gly | aca Thr | tgt Cys | aac Asn | tac Tyr 425 | tat Tyr | tca Ser | aac Asn | tcc Ser | tac Tyr 430 | agt Ser | ttc Phe | 129 |
| 1297 | tgg Trp | ttg Leu | gct Ala 435 | tca Ser | tta Leu | gac Asp | ccc Pro | aaa Lys 440 | aga Arg | atg Met | ttc Phe | aga Arg | aaa Lys 445 | cct Pro | att Ile | cca Pro | 134 |
| 1345 | tca Ser | act Thr 450 | gtg Val | aaa Lys | gct Ala | ggg Gly | gag Glu 455 | tta Leu | gaa Glu | aac Asn | ata Ile | ata Ile 460 | agt Ser | cgc Arg | tgt Cys | caa Gln | 139 |
| 1393 | gtg Val 465 | tgc Cys | atg Met | aag Lys | atg Met | aga Arg 470 | cca Pro | tga End | 1416 | | | | | | | | |

4. An isolated and substantially pure nucleotide having the following sequence SEQ. ID No. 2 of nucleotides:

| Pos | 1 | 2 | 3 | 4 | 5 | 6 | 7 | 8 | 9 | 10 | 11 | 12 | 13 | 14 | 15 | 16 | End |
|---|---|---|---|---|---|---|---|---|---|---|---|---|---|---|---|---|---|
| 1 | CAA Gln | ACA Thr | ACC Thr | GCA Ala | ATT Ile 5 | CCT Pro | TCA Ser | TGT Cys | CCA Pro | GAG Glu 10 | GGG Gly | ACA Thr | GTG Val | CCA Pro | CTC Leu 15 | TAC Tyr | 48 |
| 49 | AGT Ser | GGG Gly | TTT Phe | TCT Ser 20 | CTT Leu | TTT Phe | GTA Val | TTT Phe | CAA Gln 25 | AAT Asn | TGC Cys | GGA Gly | CAA Gln | CAC His | GCC Ala 30 | GGA Gly | 96 |
| 97 | CAA Gln | GAC Asp | CTT Leu 35 | GGA Gly | TTC Phe | TCA Ser | AGC Ser 40 | GGC Gly | CAG Gln | TGC Cys | CTG Leu | CTT Leu | TTT Phe 45 | CGA Arg | ACC Thr | ATG Met | 144 |
| 145 | CCA Pro | TTC Phe 50 | TTA Leu | TGC Cys | GAT Asp | GTC Val 55 | GTA Val | AAT Asn | AAT Asn | CCA Pro | GAT Asp 60 | CGA Arg | TTT Phe | ACA Thr | GCA Ala | ATG Met | 192 |
| 193 | AAT Asn 65 | GAT Asp | GCT Ala | TAC Tyr | ACT Thr | CTG Leu 70 | TGG Trp | TCA Ser | CTG Leu | AGA Arg | ACA Thr 75 | GCT Ala | CCA Pro | CTG Leu | ATG Met | CGA Arg 80 | 240 |
| 241 | ATG Met | ACT Thr | GGT Gly | GGC Gly | ATC Ile 85 | ACT Thr | AGA Arg | TCA Ser | GCG Ala | GCA Ala | CCT Pro 90 | GAG Glu | ATA Ile | CAC His | GGA Gly | AAC Asn 95 | 288 |
| 289 | ACT Thr | GCT Ala | GGT Gly | ATT Ile | ACA Thr | CCT Pro | TGT Cys | GCC Ala | CTT Leu | ATA Ile 100 | GCC Ala 105 | CAC His | CTC Leu 125 | GTT Val | TCT Ser | AGA Arg 95 | 336 |
| 337 | ACT Thr | GAC Asp | GAC Asp | GCT Ala | GGT Gly | CCT Pro | TGT Cys | TGG Trp | TCC Ser | ATA Ile | GGC Gly | GCA Ala 105 | ATG Met | CTG Leu | TTC Phe | AGC Ser 110 | 384 |
| 385 | TTT Phe | TCA Ser 130 | AGT Ser | GGT Gly | AGA Arg | TCC Ser | TCA Ser | CCT Pro | ACA Thr 135 | AGA Arg | TCT Ser | GAG Glu 140 | ATT Ile | GGT Gly | GCA Ala | CCA Pro | 432 |
| 433 | GCA Ala 145 | CTG Leu | CCC Pro | GCC Ala | GAA Glu | GGC Gly 150 | TCC Ser | TGC Cys | ATC Ile | TGG Trp | CAC His | TTC Phe | TAC Tyr | TTT Phe | GAA Glu 155 | CCA Pro | 480 |
| 481 | TTT Phe | CTA Leu | TTC Phe | GCC Ala | GAA Glu | GGA Gly | AAC Asn | CAT Cys 165 | TGG Trp | TGC Cys 170 | ACG Thr | TAC Tyr | TCC Ser | TAT Tyr | CCA Pro 160 | ATG Met | 528 |
| 529 | TAC Tyr | AGT Ser | AGT Ser | GCT Ala | ACT Thr | GGA Gly | TGG Trp 180 | TCA Ser | AAC Asn | ACG Thr | AAC Asn 185 | TCC Ser | TTC Phe 190 | AGA Arg | AGC Ser | AAT Asn 175 | 576 |
| 577 | CCT Pro | ATT Ile | AGT Ser | GCT Ala | GTG Val | CCA Pro 195 | GCT Ala 200 | TCA Ser | GAA Glu | GGG Gly | CCA Pro | TAT Tyr | ATG Met | AAA Lys 205 | ATA Ile | AGA Arg | 624 |
| 625 | CGC Arg | TGT Cys 210 | GTG Val | ATG Met | AAG Lys 215 | AAA Lys | AGA Arg | CAC His | TGA End | | | | | | | | 657 |

*  *  *  *  *